United States Patent
Castro et al.

(10) Patent No.: US 10,406,261 B2
(45) Date of Patent: Sep. 10, 2019

(54) BIOMIMETIC BIPHASIC 3D NANOCOMPOSITE SCAFFOLD FOR OSTEOCHONDRAL REGENERATION

(71) Applicant: The George Washington University, A Congressionally Chartered Not-For-Profit Corporation, Washington, DC (US)

(72) Inventors: Nathan J. Castro, Washington, DC (US); Christopher M. O'Brien, Washington, DC (US); Lijie Grace Zhang, Arlington, VA (US)

(73) Assignee: The George Washington University, a Congressionally Chartered Not-For-Profit Corporation, Washington, DC (US)

( * ) Notice: Subject to any disclaimer, the term of this patent is extended or adjusted under 35 U.S.C. 154(b) by 334 days.

(21) Appl. No.: 14/854,504

(22) Filed: Sep. 15, 2015

(65) Prior Publication Data
US 2016/0228611 A1 Aug. 11, 2016

Related U.S. Application Data

(63) Continuation-in-part of application No. PCT/US2014/016590, filed on Feb. 14, 2014.
(Continued)

(51) Int. Cl.
*A61L 27/48* (2006.01)
*A61L 27/58* (2006.01)
(Continued)

(52) U.S. Cl.
CPC ............. *A61L 27/48* (2013.01); *A61L 27/12* (2013.01); *A61L 27/18* (2013.01); *A61L 27/54* (2013.01); *A61L 27/58* (2013.01); *A61L 2300/414* (2013.01); *A61L 2300/624* (2013.01); *A61L 2400/08* (2013.01); *A61L 2400/12* (2013.01); *A61L 2400/18* (2013.01);
(Continued)

(58) Field of Classification Search
None
See application file for complete search history.

(56) References Cited

U.S. PATENT DOCUMENTS

| | | | |
|---|---|---|---|
| 2006/0067969 A1* | 3/2006 | Lu | A61L 27/3839 424/423 |
| 2008/0187487 A1* | 8/2008 | Larsen | A61K 9/5094 424/1.21 |
| 2010/0291178 A1* | 11/2010 | Lu | A61L 27/3839 424/423 |

OTHER PUBLICATIONS

Oberdörster et al. 2005. Principles for characterizing the potential human health effects from exposure to nanomaterials: elements of a screening strategy. Particle and Fibre Toxicology, vol. 2, No. 8, pp. 1-35.*

(Continued)

*Primary Examiner* — Thane Underdahl
(74) *Attorney, Agent, or Firm* — Venable LLP; Henry J. Daley; Miguel A. Lopez

(57) ABSTRACT

The invention describes methods for producing a biphasic nanocomposite scaffold comprising custom polymer-based core-shelled nanospheres by the physical and chemical attachment of two disparate polymeric materials whose composition can be readily modified with tissue-specific nanomaterials and products created using such methods. The custom nanospheres are constructed via co-axial wet electrospraying and can be employed to deliver compounds to the polymeric materials.

14 Claims, 30 Drawing Sheets

Related U.S. Application Data

(60) Provisional application No. 61/799,203, filed on Mar. 15, 2013, provisional application No. 61/879,021, filed on Sep. 17, 2013.

(51) Int. Cl.

| | |
|---|---|
| *A61L 27/54* | (2006.01) |
| *A61L 27/12* | (2006.01) |
| *A61L 27/18* | (2006.01) |
| *B33Y 10/00* | (2015.01) |
| *B33Y 70/00* | (2015.01) |
| *B33Y 80/00* | (2015.01) |
| *B29K 67/00* | (2006.01) |
| *B29K 71/00* | (2006.01) |
| *B29C 64/112* | (2017.01) |

(52) U.S. Cl.
CPC ....... *A61L 2420/02* (2013.01); *A61L 2420/04* (2013.01); *A61L 2430/02* (2013.01); *A61L 2430/06* (2013.01); *B29C 64/112* (2017.08); *B29K 2067/04* (2013.01); *B29K 2071/02* (2013.01); *B29K 2995/0056* (2013.01); *B33Y 10/00* (2014.12); *B33Y 70/00* (2014.12); *B33Y 80/00* (2014.12)

(56) References Cited

OTHER PUBLICATIONS

Choi et al. 2010. Fabrication of core-shell microcapsules using PLGA and alginate for dual growth factor delivery system. Journal of Controlled Release, vol. 147, pp. 193-201.*
Zhang et al "Coaxial electrospray of microparticles and nanoparticles for biomedical applications" Expert Rev Med Devices. Nov. 2012 ; 9(6): 595-612 (Year: 2012).*
Chang et al. "Controlling the thickness of hollow polymeric microspheres prepared by electrohydrodynamic atomization" J. R. Soc. Interface (2010) 7, S451-S460 (Year: 2010).*
Fu et al., miRNA Biomarkers in Breast Cancer Detection and Management. J Cancer. 2011;1(2)116-122.
Graves et al., Encapsulation of indomethacin using coaxial ultrasonic atomization followed by solvent evaporation. Drug Dev Ind Pharm. Apr. 2008;34(4):419-426.
Holmes et al., Tissue Eng Part A, 2015, 21, 403-415.
Huang et al.,BMP-2 exerts differential effects on differentiation of rabbit bone marrow stromal cells grown in two-dimensional and three-dimensional systems and is required for in vitro bone formation in a PLGA scaffold. Exp Cell Res. Oct. 1, 2004;299(2):325-334.
Hutmacher, J Biomat Sci-Polym E, 2001, 12, 107-124.
Hwang et al., Langmuir, 2008, 24, 2446-2451.
Ichinose et al., Clinical and experimental pharmacology & physiology, 2005, 32, 561-570.
Im et al., Biomimetic three-dimensional nanocrystalline hydroxyapatite and magnetically synthesized single-walled carbon nanotube chitosan nanocomposite for bone regeneration. Int J Nanomedicine. 2012;7:2087-2099.
Iwatsubo et al.,Biomacromolecules, 2006, 7, 95-100.
Kalfa et al., A polydioxanone electrospun valved patch to replace the right ventricular outflow tract in a growing lamb model. Biomaterials. May 2010;31(14):4056-4063.
Karageorgiou et al., Biomaterials, 2005, 26, 5474-5491.
Karande et al., Annals of Biomedical Engineering, 2004, 32, 1728-1743.
Kim et al., Bone regeneration using hyaluronic acid-based hydrogel with bone morphogenic protein-2 and human mesenchymal stem cells. Biomaterials. Apr. 2007;28(10):1830-1837.
Kim et al., Transient exposure to TGF-beta3 improves the functional chondrogenesis of MSC-laden hyaluronic acid hydrogels. Journal of the mechanical behavior of biomedical materials. Jul. 2012;11:92-101.
Kim et al., Bone morphogenic protein-2 (BMP-2) immobilized biodegradable scaffolds for bone tissue engineering. Macromol Res. Oct. 2006;14(5):565-572.
Knychala et al., Ann Biomed Eng, 2013, 41, 917-930.
Kwon et al., Modulation of BMP-2-induced chondrogenic versus osteogenic differentiation of human mesenchymal stem cells by cell-specific extracellular matrices. Tissue Eng Part A. Jan. 2013;19(1-2):49-58.
Li et al., International Journal of Smart and Nano Materials, 2011, 3, 2-13.
Lin-Gibson et al., Biomacromolecules, 2007, 8, 1511-1518.
Liu et al., Biodegradation, biocompatibility, and drug delivery in poly(ω-pentadecalactone-co-p-dioxanone) copolyesters. Biomaterials. 2011;32(27):6646-6654.
Madhumathi et al., International journal of biological macromolecules, 2009, 45, 12-15.
Madurantakam et al., Multiple factor interactions in biomimetic mineralization of electrospun scaffolds. Biomaterials. Oct. 2009;30(29):5456-5464.
Makadia et al., Polymers, 2011, 3, 1377-1397.
Marchesi, Eur Spine J, 2000, 9, 372-378.
Matsumura et al., *J Biomed Mater Res A*, 2009, 92, 1225-1232.
Moreau et al., *Biomatter*, 2014, 4, e28764.
Murphy et al., *J Biomed Mater Res A*, 2013, 101A, 272-284.
Noel et al., Short-term BMP-2 expression is sufficient for in vivo osteochondral differentiation of mesenchymal stem cells. Stem Cells. 2004;22(1):74-85.
O'Brien et al., *Tissue Eng Part B Rev*, 2014.
Ozkan et al., *J Biomed Mater Res Part A*, 2009, 92, 1007-1018.
Ozkan et al., *Biomaterials*, 2009, 30, 4336-4347.
Panusa et al., Methylprednisolone-loaded PLGA microspheres: a new formulation for sustained release via intra-articular administration. A comparison study with methylprednisolone acetate in rats. J Pharm Sci. Nov. 2011;100 (11):4580-4586.
Piconi and G. Maccauro, *Biomaterials*, 1999, 20, 1-25.
Place et al., *Chemical Society reviews*, 2009, 38, 1139-1151.
Sakamoto et al., An investigation of the fixation materials for cartilage frames in microtia. Journal of plastic, reconstructive & aesthetic surgery : JPRAS. May 2012;65(5):584-589.
Schagemann et al., J Biomed Mater Res A, 2012, 101, 1620-1628.
Sekiya et al., BMP-6 enhances chondrogenesis in a subpopulation of human marrow stromal cells. Biochem Biophys Res Commun. Jun. 8, 2001;284(2):411-418.
Sibilla et al., J Dent Res, 2006, 85, 354-358.
Smith et al., Suture-reinforced electrospun polydioxanone-elastin small-diameter tubes for use in vascular tissue engineering: a feasibility study. Acta Biomater. 2008;4:58-66.
Smith et al., Wiley Interdisciplinary Reviews—Nanomedicine and Nanobiotechnology, 2009, 1, 226-236.
Solorio et al., Chondrogenic differentiation of human mesenchymal stem cell aggregates via controlled release of TGF-beta1 from incorporated polymer microspheres. J Biomed Mater Res A. Mar. 1, 2010;92(3):1139-1144.
Sopyan et al., Science and Technology of Advanced Materials, 2007, 8, 116-123.
Stevanovic M, Uskokovic D. Poly(lactide-co-glycolide)-based Micro and Nanoparticles for the Controlled Drug Delivery of Vitamins. Curr Nanosci. Feb. 2009;5(1):1-14.
Sugino et al., Journal of materials science. Materials in medicine, 2008, 19, 2269-2274.
Sun et al., Biomaterials, 2013, 34: 4971-4981.
Tang et al., J Biomat. Sci., 2012, 23, 2241-2257.
Tarafder et al., Electrically polarized biphasic calcium phosphates: adsorption and release of bovine serum albumin. Langmuir. Nov. 16, 2010;26(22):16625-16629.
Tezcan et al., Dose dependent effect of C-type natriuretic peptide signaling in glycosaminoglycan synthesis during TGF-beta1 induced chondrogenic differentiation of mesenchymal stem cells. Journal of molecular histology. Oct. 2010;41(4-5):247-258.

(56) References Cited

OTHER PUBLICATIONS

Almeria et al., Controlling the morphology of electrospray-generated PLGA microparticles for drug delivery. J Colloid Interface Sci. Mar. 1, 2010; 343(1):125-133.
Arcaute K, Mann BK, Wicker RB. Stereolithography of three-dimensional bioactive poly(ethylene glycol) constructs with encapsulated cells. Ann Biomed Eng. Sep. 2006; 34(9):1429-1441.
Bai X, Li G, Zhao C, Duan H, Qu F. BMP7 induces the differentiation of bone marrow-derived mesenchymal cells into chondrocytes. Med Biol Eng Comput. Jun. 2011; 49(6):687-692.
Baji et al., *Mater Manuf Process*, 2006, 21, 211-218.
Bian, et al., *Rapid Prototyping J*, 2012, 18, 68-80.
Bouffi et al., The role of pharmacologically active microcarriers releasing TGF-beta3 in cartilage formation in vivo by mesenchymal stem cells. Biomaterials. Sep. 2010; 31(25):6485-6493.
Castro N, Hacking S, Zhang L. Recent Progress in Interfacial Tissue Engineering Approaches for Osteochondral Defects. Ann Biomed Eng. 2012; 40(8):1628-1640.
Castro, C. M. O'Brien and L. G. Zhang, *Aiche J*, 2014, 60, 432-442.
Castro, R. Patel and L. Zhang, *Cellular and Molecular Bioengineering*, 2015, 1-17.
Chim et al., Stromal-cell-derived factor (SDF) 1-alpha in combination with BMP-2 and TGF-beta1 induces site-directed cell homing and osteogenic and chondrogenic differentiation for tissue engineering without the requirement for cell seeding. Cell Tissue Res. Oct. 2012; 350(1):89-94.
Collins et al.,Charge generation, charge transport, and residual charge in the electrospinning of polymers: A review of issues and complications. Journal of Applied Physics 2012, 111(4).
Colter et al.,Rapid expansion of recycling stem cells in cultures of plastic-adherent cells from human bone marrow. Proc Natl Acad Sci U S A. Mar. 28, 2000; 97(7):3213-3218.

Davis et al.,Osteogenic Response to BMP-2 of hMSCs Grown on Apatite-Coated Scaffolds. Biotechnol Bioeng. Nov. 2011; 108(11):2727-2735.
Dawes et al.,Size effect of PLGA spheres on drug loading efficiency and release profiles. Journal of materials science. Materials in medicine. May 2009; 20(5):1089-1094.
Dawes et al.,Release of PLGA-encapsulated dexamethasone from microsphere loaded porous surfaces. Journal of materials science. Materials in medicine. Jan. 2010; 21(1):215-221.
Dawson et al.,Biomaterials, 2008, 29, 3105-3116.
De Boer et al.,In vitro and in vivo release of nerve growth factor from biodegradable poly-lactic-co-glycolic-acid microspheres. J Biomed Mater Res A. Dec. 15, 2010; 95(4):1067-1073.
Elisseeff et al.,Langer R. Controlled-release of IGF-I and TGF-beta1 in a photopolymerizing hydrogel for cartilage tissue engineering. J Orthop Res. Nov. 2001; 19(6):1098-1104.
Ergun, X. Yu, A. Valdevit, A. Ritter and D. M. Kalyon, J Biomed Mater Res A, 2011, 99, 354-366.
Ergun et al.,Tissue engineering. Part A, 2012, 18, 2426-2436.
Erisken, D. M. Kalyon and H. Wang, Biomaterials, 2008, 29, 4065-4073.
Erisken, D. M. Kalyon and H. Wang, J Biomech Eng, 2010, 132, 091013.
Erisken, D. M. Kalyon and H. Wang, Nanotechnology, 2008, 19, 165302.
Ertan AB, Yilgor P, Bayyurt B, et al. Effect of double growth factor release on cartilage tissue engineering. Journal of tissue engineering and regenerative medicine. Nov. 14, 2011.
Friedman et al.,Journal of Biomedical Materials Research, 1998, 43, 428-432.

\* cited by examiner 1000 mm/min     1500 mm/min     2000 mm/min

BIOMIMETIC BIPHASIC 3D NANOCOMPOSITE SCAFFOLD FOR OSTEOCHONDRAL REGENERATION

CROSS-REFERENCE TO PRIOR APPLICATIONS

This application is a continuation-in-part of PCT/US2014/016590 which was filed on Feb. 14, 2014, which claims priority to U.S. provisional patent application 61/799,203 filed on Mar. 15, 2013 and U.S. provisional patent application 61/879,021 filed on Sep. 17, 2013, the entire contents of each is hereby incorporated herein by reference.

U.S. GOVERNMENT SUPPORT

This invention was made with Government support of Grants No. UL1RR031988 and DP2EB020549, awarded by NIH. The U.S. Government has certain rights in this invention.

FIELD OF THE INVENTION

The present invention relates to a novel method for physical and chemical attachment of two disparate polymeric materials whose composition can be readily modified with tissue-specific nanomaterials. In some embodiments, custom nanospheres can be employed to deliver active compounds to the polymeric materials.

BACKGROUND OF THE INVENTION

Tissue engineering is an example of an area where the attachment of disparate biomaterials is of interest. Tissue engineering and regenerative medicine approaches have been extensively employed to treat conditions (such as single-tissue orthopedic defects) through the use of functional biomimetic biomaterials,[1-5] with more emphasis towards the interface.[6]

Although the interdisciplinary field of tissue engineering holds great promise for the treatment of numerous conditions, various serious limitations remain that prevent the effective use of current techniques in the regeneration of certain tissues. For instance, the regeneration of cartilage by current tissue engineering approaches has proven to be challenging because cartilage has a very limited regenerative capacity. Articular cartilage in joints is relatively avascular, contains few native mature cells (chondrocytes) and possesses a gradient of properties from the synovial surface to the subchondral bone. These characteristics are distinctly different from the highly vascularized and heavily cell populated composition of bone. In addition, there is a complex interface between cartilage and subchondral bone. The treatment of damaged tissues at interfaces, like the osteochondral interface, is particularly difficult due to the presence of biological and chemical gradients, namely: cell population(s), tissue type, and extracellular matrix (ECM) proteins are often present and difficult to recapitulate. The osteochondral interface is of great importance since it is a site of attachment between two distinct tissues while providing the necessary structure and mechanical integrity for energy transfer.

Interfacial tissue engineering (ITE) is one approach to address the complex bi- or multiphasic nature of osteochondral defects. This serves to introduce the main caveat of ITE, where interfaces have shared characteristics of the tissues being connected but also contains regions of distinct composition and biological function.[7] As a result, the development of new methods, biomaterials, and techniques to manufacture biomimetic constructs linking two distinct tissues within certain biological and mechanical constraints presents considerable challenges. In addition, it is important to note that natural human osteochondral tissue ECM is in the nanometer dimension range and is composed of many nanostructured components (such as nanocrystalline hydroxyapatites, collagen and various other proteins).[8]

SUMMARY OF THE INVENTION

The present invention relates to a novel method for physical and chemical attachment of two disparate polymeric materials whose composition can be readily modified with tissue-specific nanomaterials. In some embodiments, custom nanospheres constructed via co-axial wet electrospraying can be employed to deliver compounds, solutions or agents to the polymeric materials. In other embodiments, this method can also be used in the construction of biphasic nanocomposite scaffolds. In some embodiments, these scaffolds can be biomimetic, biphasic nanocomposite scaffolds that can be used for the regeneration of specific tissues and overcome the limitations of current biomimetic tissue engineering techniques.

In exemplary embodiments, the method is used for the generation of a biphasic biomimetic nanocomposite scaffold to provide sustained biological cues for enhanced human bone marrow-derived mesenchymal stem cell (hMSC) differentiation and new tissue formation. In exemplary embodiments, co-axial wet electrospray technique is used in a novel way to manufacture growth factor-encapsulated core-shell nanospheres, allowing for efficient encapsulation of tissue-specific growth factors within a wide range of biodegradable polymers. This overcomes limitations of traditional emulsion-based micro-sphere or nano-sphere fabrication techniques, wherein limitations regarding initial burst and uncontrolled release have inhibited their full clinical potential due to the disparity in particle size. The co-axial wet electrospray technique developed in the exemplary embodiment produces nanospheres with good size distribution aiding in more controlled growth factor release. In exemplary embodiments, the generated biphasic biomimetic nanocomposite scaffold provides improved osteochondral regeneration and overcomes limitations of current biomimetic tissue engineering techniques. It also meets a long felt need for an effective method for regeneration of tissues (such as cartilage) that have limited regenerative capacity. The application of the technique in the exemplary model provided should not be considered to limit the application of the invention in terms of other applications. One of ordinary skill in the art will readily understand that this technique can be used to replicate the tissues of any interface where two or more distinct types of tissues meet. In this sense, a tissue can be interpreted as tissue that is made up of epithelial cells, muscle cells, connective tissue cells, nerve cells or blood cells.

Further objectives and advantages, as well as the structure and function of preferred embodiments will become apparent from a consideration of the description, and non-limiting examples that follow.

DESCRIPTION OF THE FIGURES

Exemplary embodiments of the invention will be now described in greater detail below with reference to the accompanying drawings, in which:

FIG. 2A shows bone layer preparation; FIG. 2B shows cartilage layer preparation.

DETAILED DESCRIPTION OF THE INVENTION

Figure 1A:
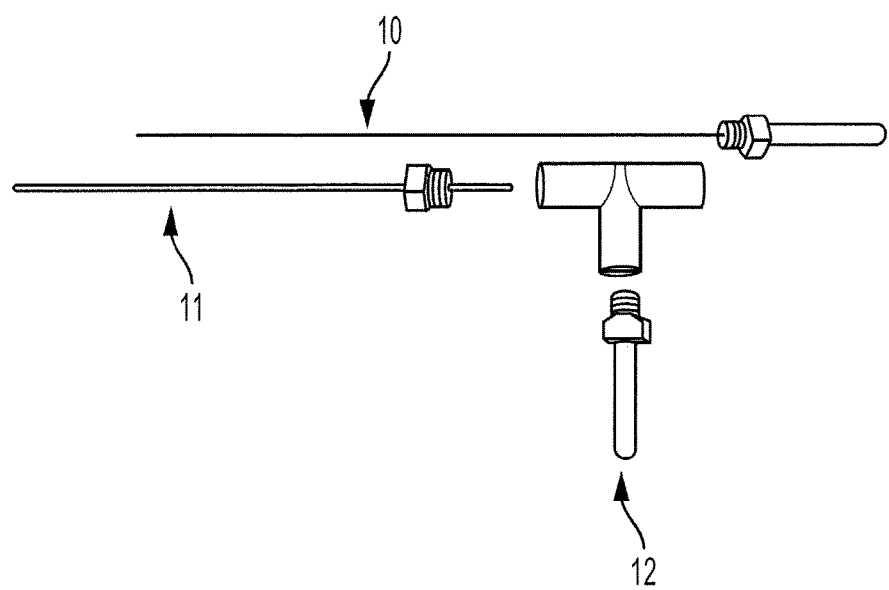
FIG. 1A shows a co-axial electrospray system used in the manufacture of growth factor encapsulated polymeric nanospheres.

Embodiments of the invention are discussed in detail below. In describing embodiments, specific terminology is employed for the sake of clarity. However, the invention is not to be limited to the specific terminology so selected. While specific exemplary embodiments are discussed, it should be understood that it is for illustration purposes only. A person skilled in the art will recognize that other components and configurations can be used without parting from the spirit and scope of the invention. All references cited herein are incorporated by reference as if each had been individually incorporated to the extent permitted by applicable law and regulation.

As the leading cause of disability in the United States, osteoarthritis (OA) is a degenerative disease that manifests clinically as a loss of the articular surface in synovial joints resulting in discomfort, chronic pain, and loss of movement. Damage from osteoarthritis can range from a moderate reduction in thickness of hyaline cartilage, to near-complete erosion of the cartilage to the point where subchondral bone is exposed. As of 2006, over 48 million Americans were afflicted with osteoarthritis or some form of degenerative joint disease, and the number is expected to increase to 67 million Americans by 2030.[9] People with this disease experience reduced joint mobility and severe pain due to the gradual loss or traumatic injury to the articular cartilage and subchondral bone which is collectively known as osteochondral tissue. As the osteochondral tissue degrades, the connective tissue holding the joint together stretches, further increasing the pain felt by patients. Compounding the damage, articular cartilage is not highly vascularized, and depends on diffusion of gases and nutrients from the subchondral bone.

Current treatment methods used to address these defects include autografts, allografts, and mosaicplasties. Each of these methods contains its own inherent limitations, including donor site morbidity, infection, poor tissue integration, and neovascularization, which continue to prevent the clinical success of these traditional methods. Even autografts, which are considered the gold standard for repairing this kind of defect, have limitations; particularly in older patients whose cell activity may be low. Extensive research employing tissue engineering approaches have focused on regenerating both tissues independently with good results. In severe cases, total joint arthroplasty is suggested as a treatment. This invasive procedure replaces the articular surface with synthetic materials. Although it is considered a successful treatment, complications can arise including infection, osteolysis, and adverse reaction to metal ions can affect the longevity of the implant. Due to the complex mechanical nature of the osteochondral site, single-material biomimetic constructs lack the dynamic range necessary to repair the interface of such distinctly different tissues. For example, osteochondral sites are often subject to repetitive, complex compressive loads which prove difficult for any single biomaterial to respond to appropriately as the natural material does. Protein and different tissue types have a gradient that needs to be adequately reproduced within one construct without compromising the tight integration of the two distinctly difficult tissue types. The sheer complexity of engineering an interface between vastly different tissues leads one to believe that no single material can adequately reproduce the physiological and mechanical properties.

As a result, the development of novel biomimetic tissue engineered (TE) constructs for the treatment of OA is of pressing interest. Tissue engineering and regenerative medicine approaches have been extensively employed in addressing single-tissue orthopedic defects through the use of functional biomaterials[2-5] with more emphasis directed towards the interface[6]. The interdisciplinary field of TE holds great promise for the development of novel therapeutic approaches for the treatment of traumatic injuries, diseases and congenital defects that overcome the body's natural healing capacity.[10] The regeneration of cartilage by TE approaches has proven to be challenging since cartilage has a very limited regenerative capacity. Articular cartilage in joints is relatively avascular, contains few native mature cells (chondrocytes) and possesses a gradient of properties from the synovial surface to the subchondral bone. These characteristics are distinctly different from the highly vascularized and heavily cell populated composition of bone. In addition, there is a complex interface between cartilage and subchondral bone. The treatment of damaged tissues at interfaces, like the osteochondral interface, is particularly difficult due to the presence of biological and chemical gradients, namely: cell population(s), tissue type, and extracellular matrix (ECM) proteins are often present and difficult to recapitulate. In this instance, the extracellular matrix means extracellular material that may or may not be secreted by cells and may or may not consist of protein fibers embedded in an amorphous mixture of protein-polysaccharide molecules. The osteochondral interface is of great importance since it is a site of attachment between two distinct tissues while providing the necessary structure and mechanical integrity for energy transfer.

Interfacial tissue engineering (ITE) is one approach to address the complex bi- or multiphasic nature of osteochondral defects. The main caveat of ITE is where interfaces have shared characteristics of the tissues being connected but also contains regions of distinct composition and biological function.[7] As a result, the development of new methods, biomaterials, and techniques to manufacture biomimetic constructs linking two distinct tissues within certain biological and mechanical constraints presents considerable challenges. In addition, it is important to note that natural human osteochondral tissue ECM is nanometer in dimension and composed of many nanostructured components (such as nanocrystalline hydroxyapatites, collagen and various other proteins).[8] Thus, one objective of this study was to develop a biphasic biomimetic nanocomposite scaffold to provide sustained biological cues for enhanced human bone marrow-derived mesenchymal stem cell (hMSC) differentiation and new tissue formation.

In particular, one of the novel features of the biphasic osteochondral scaffold developed herein is the use of co-axial wet electrospray in the manufacture of growth factor-encapsulated core-shell nanospheres allowing for efficient encapsulation of tissue-specific growth factors within a wide range of biodegradable polymers. Traditional emulsion-based micro-sphere or nano-sphere fabrication techniques have exhibited positive results, but limitations regarding initial burst and uncontrolled release have inhibited their full clinical potential due to the disparity in particle size. The co-axial wet electrospray technique developed herein has been demonstrated to produce nanospheres with good size distribution aiding in more controlled growth factor release.

In addition to core-shell nano-sphere fabrication, a photocurable co-porogen system was used in creating the biomimetic biphasic nanocomposite construct as a means of physically and chemically attaching the two distinctly different biomaterials, poly(caprolactone) (PCL) and poly(ethylene glycol) (PEG)). Therefore, the current work has developed an efficient wet electrospray growth factor nano-sphere technique, as well as a novel biphasic osteochondral nanocomposite scaffold for directed and enhanced human MSC differentiation.

The example provided below should not be considered to limit the application of the invention for the creation of other multi-phasic constructs replicating other multi-phasic environments where two or more tissues interface. In addition, scaffolds employed can be made up of any inert material (synthetic or not) and additionally tissues. Nanoparticles can be used to deliver compounds into the multi-phasic construct (as in the case of the example), or not. Nanoparticles can also be made up of inert materials, synthetic or not.

EXAMPLES

Example 1: Biomimietic Biphasic 3D Nanocomposite Scaffold for Osteochondral Regeneration Scaffold-based ITE aims to not only provide the structural and mechanical framework for cellular growth and tissue regeneration, but also control cell adhesion, proliferation and differentiation. Due to the disparity in composition and mechanical properties of the osteochondral (cartilage and bone) interface, the current work has developed a novel biomimetic biphasic nanocomposite osteochondral scaffold integrating two biocompatible polymers containing tissue-specific growth factor-encapsulated core-shell nanospheres. Specifically, a poly(caprolactone) (PCL)-based bone layer was successfully integrated with a poly(ethylene glycol) (PEG) hydrogel cartilage layer. In addition, the current work developed a novel nano-sphere fabrication technique for efficient growth factor encapsulation and sustained delivery via wet co-axial electrospray. Human bone marrow mesenchymal stem cell (hMSC) adhesion, osteogenic and chondrogenic differentiation were evaluated in our constructs. Our in vitro results showed significantly improved hMSC adhesion and differentiations in bone and cartilage layers, respectively. Our studies have demonstrated promising results with our novel biphasic nanocomposite scaffold for osteochondral tissue regeneration, thus warranting further studies.

Materials and Methods

PLGA/PDO Wet Electrosprayed Nanosphere Fabrication and Characterization

Poly(dioxanone) (PDO) (Sigma-Aldrich, St. Louis, Mo.) and poly(lactic-co-glycolic) acid (PLGA) (Lactel Absorbable Polymers, Birmingham, Ala.) nanospheres were fabricated by co-axial wet electrospray via a custom co-axial needle system as shown in FIG. 1a composed of a 26G inner needle, 10, (304SS 0.018" outer diameter (OD), 0.01" inner diameter (ID)) receded within a 20G needle, 11, (304SS 0.036" OD, 0.0275" ID) (McMaster-Carr, Robbinsville, N.J. 08691). The inter needle spacing is 0.0095". 12, is a 12 gauge needle.

Figure 1B:
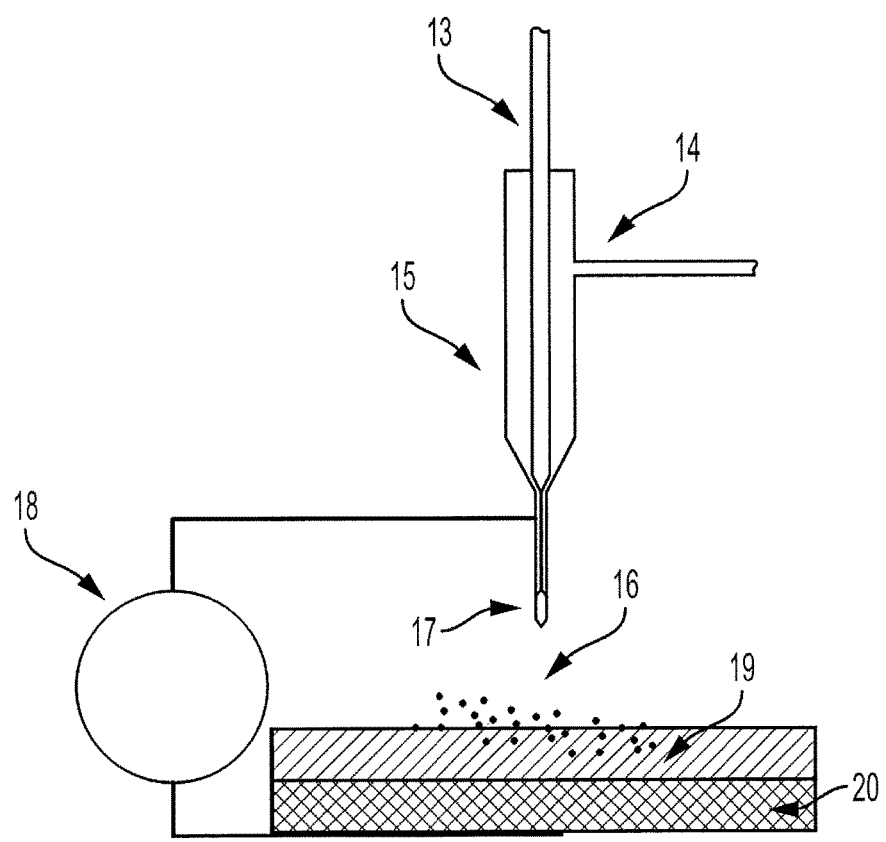
FIG. 1B is a schematic showing encapsulated nanospheres being fed through the electrospray system.

Briefly, bone morphogenic protein-2 (BMP-2) and transforming growth factor-β1 (TGF-β1) (PeproTech, Rocky Hill, N.J.) lyophilized powders were resuspended per manufacturer's instructions and working concentrations of 10 ng/mL were used in all experiments. For BMP-2 encapsulated PDO nanospheres, a 2.5% (weight/weight %) solution of PDO in 1,1,1,3,3,3-hexafluoropropanol (HFIP) (Sigma-Aldrich, St. Louis, Mo.) was fed through the shell feed inlet (FIG. 1b, 14) at a flow rate of 4.0 mL/hr. BMP-2 was fed through the core feed inlet, 13, at the same flow rate. Voltage within an area of high voltage potential, 18, was adjusted during collection to prevent fiber formation and maintain adequate Taylor cone, 17, morphology. An adequate Taylor cone is formed when, "At the capillary tip, the electric field puts a stress on the charged (polymer) solution and distorts it into a cone-like shape known as the Taylor cone. At a sufficiently high potential difference, the electrostatic stresses overcome the surface tension of the Taylor cone. Then, a stream of polymer fluid forms a filament (or jet stream) that traverses the distance from the Taylor cone at the capillary tip to the grounded target, the solvent component is lost by evaporation processes and the remaining polymer solidifies into a filament (or in our case a film on the collecting solution surface)."[50] Voltage used was within a range of 8-10 or 15-18 kV. Similarly, TGF-β1 encapsulated PLGA nanospheres were fabricated using the same concentrations and flow rates wherein acetone was used as the solvent. Other components of the system include a coaxial spinneret, 15, and a ground collector plate, 20.

PDO nanospheres were collected in a chloroform stabilizing bath 19, to assist in the prevention of agglomeration which was replenished periodically during electrospraying. In this case, the collecting solution was ACS grade chloroform (Sigma-Aldrich Cat#437581). PLGA nanospheres were collected in an ultrapure water stabilizing bath. In this case, the ultrapure water was collected from a Millipore RIOS UV purification system. After collection, the baths were transferred to centrifuge tubes and ultrasonicated for 30 seconds (Ultrasonicator, QSonica, Newtown, Conn.). Emulsified samples were then immediately frozen and lyophilized for 24 hours to remove the stabilizing bath prior to use.

Synthesized core-shell growth factor encapsulated nanosphere morphologies were characterized by transmission electron microscope (TEM). Particle size analysis of nanospheres was conducted with ImageJ software. Briefly, a calibrated TEM micrograph was imported in to the software and converted to a binary image with adjusted threshold to remove noise and background. Particle analysis of the binary image was conducted and particle diameters were extrapolated from calculated areas.

Encapsulation Efficiency and Release Studies of Protein Encapsulated Nanospheres Release profiles of bovine serum albumin (BSA) encapsulated PDO and PLGA nanospheres were conducted. BSA is a commonly used protein employed as an easily quantifiable and reliable model for release kinetics examination. PDO and PLGA nanospheres were prepared as described above with a working solution of 1% BSA (weight/volume) in ultrapure water. Lyophilized nano-sphere samples were incubated in PBS under standard culture conditions for up to 18 days. Samples were pelleted and the supernatant was stored for analysis. Collected fractions and standards were analyzed spectrophotometrically (MicroBCA® Protein Kit, Fisher Thermo Scientific, Waltham, Mass.). Encapsulation efficiency of collected samples was analyzed by dissolving a known mass of collected sample in HFIP (PDO) and acetone (PLGA), respectively, and measuring absorbance of BSA at 280 nm.

Hydrothermally Treated Nanocrystalline Hydroxyapatite (nHA) Synthesis

A wet chemistry method plus a hydrothermal treatment as described in our previous papers[5, 11, 12] was used to synthesize nanocrystalline hydroxyapatite. Briefly, a 0.6 M ammonium phosphate (Sigma Aldrich, St. Louis, Mo.) solution was added to water and adjusted to a pH of 10 with ammonium hydroxide (Fisher Scientific, Pittsburgh, Pa.). A 1 M calcium nitrate (Sigma Aldrich, St. Louis, Mo.) solution was slowly titrated into the above mixture while stirring. Precipitation of HA continued for 10 min at room temperature. The solution with HA amorphous precipitate was treated hydrothermally at 200° C. for 20 h in a 125 ml Teflon liner (Parr Instrument Company, Moline, Ill.) to produce nHA. The resultant nHA was centrifuged and rinsed thoroughly with water then dried at 80° C. for 12 h. Dried nHA was ground with a ceramic pestle and mortar and run through a <150 μm sieve. Synthesized nHA particles were gold sputter-coated and imaged via scanning electron microscopy (SEM).

Biphasic (PCL/PEG-Da) Osteochondral Scaffold Fabrication and Characterization

Figure 2A:
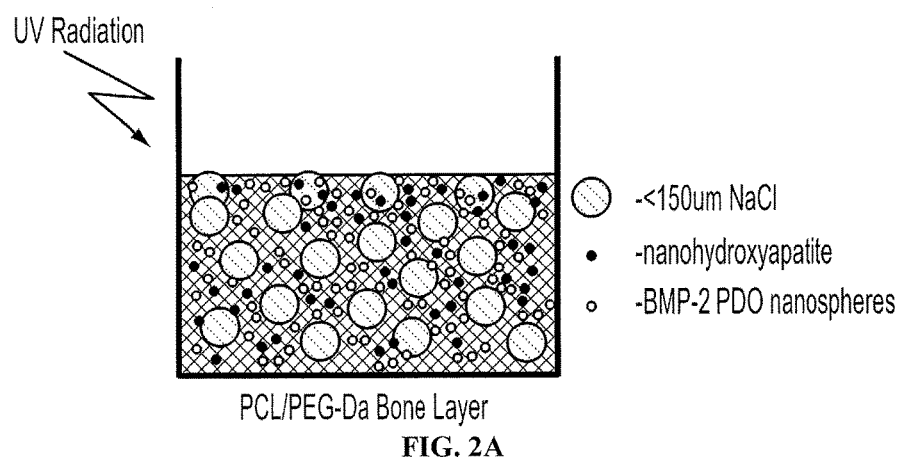
FIG. 2A and FIG. 2B show photos crosslinking/Coporogen leaching method for the fabrication of biphasic biomimetic osteochondral scaffolds.
Figure 2B:
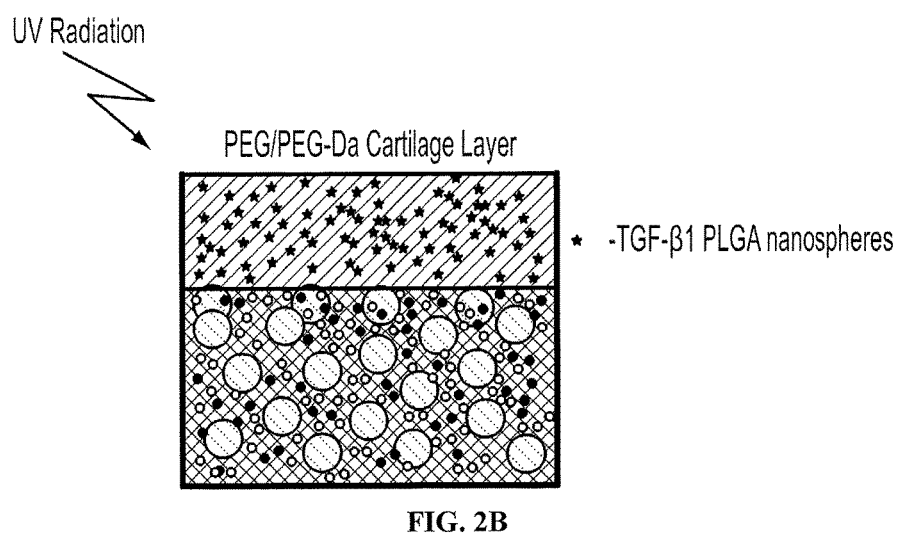

Biphasic osteochondral scaffolds were fabricated via a novel photocrosslinking/co-porogen leaching method for integration of two disparate polymeric materials as illustrated in FIG. 2. Scaffolds were prepared as a proof of concept and each layer was evaluated separately for respective hMSC differentiation.

Bone layer preparation (FIG. 2a): PCL was employed as the base bone layer material in the current system. It was dissolved in an excess of chloroform to allow for efficient mixing of all composite materials with PCL resultantly constituting 38% of the total mass of the bone layer. nHA (20% (weight/weight)) was added to the dissolved PCL. Separately, a 60:40 mixture of Poly(ethylene glycol) (PEG, Mn=300):Poly(ethylene glycol)-diacrylate (PEG-Da, Mn=700) was prepared. A photoinitiator, Bis(2,4,6-trimethylbenzoyl)-phenylphosphineoxide (BAPO) (BASF, Florham Park, N.J.), with excitation in the ultraviolet (UV) range was added to the PEG:PEG-Da mixture at 0.5 weight/weight % of PEG-Da and allowed to rest overnight for adequate dissolution. Several samples were prepared (Table 1) and used for further hMSC differentiation studies. PDO nanospheres were added to the dissolved PCL/nHA mixture. Upon complete dissolution of the photoinitiator, both PCL and PEG solutions were mixed and mechanically stirred. For hMSC differentiation experiments, complete PCL/PEG mixture was cast in to a glass petri dish allowed to rest for 10 minutes and cured for 30 seconds under UV light. 5 mm samples of crosslinked samples were collected with a biopsy punch and leached in ultrapure water for 3 days with periodic exchange of fresh ultrapure water.

TABLE 1

PCL Bone Layer Sample Composition

|  | Control | nHA | Blended BMP-2/nHA | BMP-2 spheres/nHA |
|---|---|---|---|---|
| PCL (wt %) | 38% | 38% | 38% | 38% |
| PEG:PEG-Da (wt %) | 38% | 38% | 38% | 38% |
| NaCl (<150 μm) (wt %) | 24% | 24% | 24% | 24% |
| nHA | — | 20 wt % of PCL | 20 wt % of PCL | 20 wt % of PCL |
| PDO nanospheres | — | — | — | 500 μg/g of PCL |
| BMP-2 (10 ng/mL) | — | — | 67 μL | — |

Cartilage layer preparation (FIG. 2b): For more efficient layer integration, the same 60:40 PEG:PEG-Da mixture served as the base material for all cartilage layer samples. As previously described, 0.5% (weight/weight) BAPO was added to the PEG:PEG-Da mixture and allowed to rest overnight. Lyophilized TGF-β1 encapsulated PLGA nanospheres were subsequently added and mixed for adequate dispersion within the hydrogel matrix. The hydrogel mixture was then cast in to a 9 cm glass petri dish and UV cured for 15 seconds. Fabricated cartilage layer samples used in hMSC differentiation studies can be found in Table 2. 5 mm samples of crosslinked samples were collected with a biopsy punch. Sol fraction and swelling ratios of prepared hydrogel samples were evaluated as described.[3]

TABLE 2

PEG-Da Cartilage Layer Sample Composition

|  | Control | Blended TGF-β1 | TGF-β1 spheres |
|---|---|---|---|
| PEG:PEG-Da | 100% | 100% | 100% |
| PLGA nanospheres | — | — | 500 μg/g of PEG-Da |
| TGF-β1 (10 ng/mL) | — | 67 μL | — |

Figure 2C:
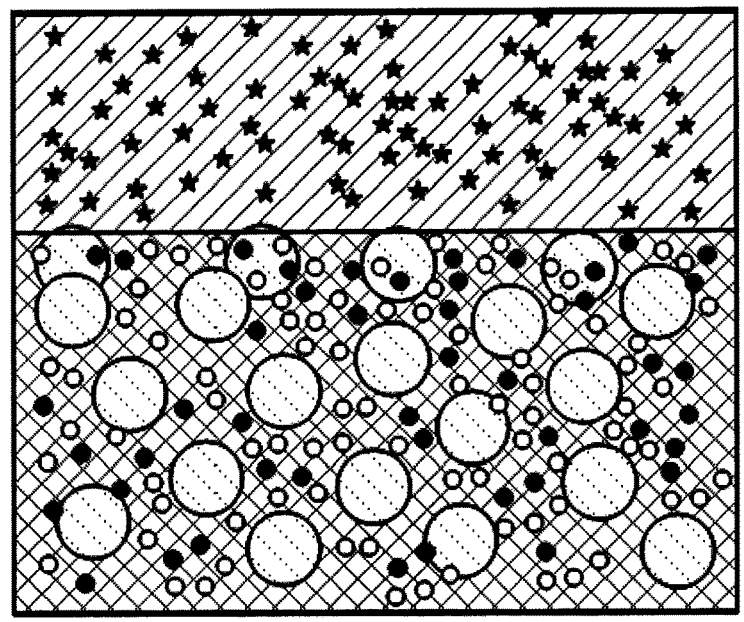
FIG. 2C shows biphasic biomimetic osteochondral scaffold preparation.

Osteochondral scaffold fabrication: Biphasic biomimetic osteochondral scaffolds were prepared as depicted in FIG. 2c. Briefly, the complete PCL/PEG-Da bone layer mixture was cast in to a 9 cm glass petri dish and allowed to rest for 5 minutes prior to partial (15 sec) UV curing. The solvent (chloroform) was allowed to partially evaporate prior to casting of the PEG-Da cartilage layer mixture. The PEG-Da cartilage layer was cast directly on top of the partially cured PCL bone layer and UV cured for 1 min. Biphasic scaffolds were sputter-coated with gold and imaged via focused ion beam operating in SEM mode (SEM, Zeiss NVision 40 FIB, Thornwood, N.Y.).

Bone/cartilage protein release: Release profiles for each respective layer and composition were evaluated. Briefly, scaffolds containing 1 mg/mL BSA were fabricated as described in Tables 1 and 2. 5 mm samples (n=6) were incubated in PBS at 37° C. and 5% CO2. Fractions of the supernatant were centrifuged, collected, and BSA content was measured spectrophotometrically at predetermined time points. Protein release profiles were plotted as a fraction of total encapsulated protein.

Mechanical testing of biphasic nano osteochondral constructs: The elastic modulus of fabricated biphasic nanocomposite scaffolds was determined via unconfined compression testing (n=3) (Applied Test Systems, Butler, Pa.) fitted with a 500N load cell at a crosshead speed of 1.2 cm/min. Samples were collected with a 5 mm biopsy punch, swollen for 48 hours with intermittent exchange of fresh ultrapure water and blotted dry prior to testing.

hMSC Study In Vitro

Primary hMSCs were obtained from healthy consenting donors from the Texas A&M Health Science Center, Institute for Regenerative Medicine and thoroughly characterized[14] Primary hMSCs (passage #3-6) were cultured in complete media composed of Alpha Minimum Essential medium (α-MEM, Gibco, Grand Island, N.Y.) supplemented with 16.5% fetal bovine serum (Atlanta Biologicals, Lawrenceville, Ga.), 1% (volume/volume) L-Glutamine (Invitrogen, Carlsbad, Calif.), and 1% penicillin:streptomycin (Invitrogen, Carlsbad, Calif.) and cultured under standard cell culture conditions (37° C., a humidified, 5% CO2/95% air environment). All of the samples were sterilized in 70% ethanol for 30 min then washed 3 times for 5 min in phosphate-buffered saline (PBS) before cell seeding.

hMSC adhesion study: Bone layer scaffolds with 0%, 10%, and 20% concentrations of nHA, PDO nanosphere and 20% nHA/PDO nano-sphere were tested in the first cell adhesion study. hMSCs were seeded at 50,000 cells/scaffold. The seeded scaffolds were then incubated under standard cell culture conditions for 4 hours. After rinsing with PBS, the adherent cells were quantified via a CellTiter 96® AQueous Non-Radioactive Cell Proliferation Assay (MTS assay) and analyzed using a Thermo Scientific Multiskan GO Spectrophotometer at a setting of 490 nm wavelength light.

hMSC osteogenic differentiation study: hMSCs were seeded at a density of 105 cells/scaffold for osteogenic differentiation evaluation. Cell seeded bone layer scaffolds were cultured in complete media supplemented with osteogenic factors (10 nM Dexamethasone, 20 mM β-glycerophosphate, and 50 μM L-Ascorbic acid) for 1 and 2 weeks, respectively.

Calcium deposition, one of the most important indicators of osteogenic differentiation, was measured using a calcium reagent kit (Pointe Scientific Inc.). Briefly, hMSCs were lysed through three freeze-thaw cycles and removed. The scaffolds containing deposited calcium and ECM were immersed in a 0.6 N HCl solution at 37° C. for 24 h. After the prescribed time period, the amount of dissolved calcium present in the acidic supernatant was measured by reacting with the o-cresolphthalein complexone to form a purple tinted solution. Absorbance was measured by a spectrophotometer at 570 nm. Total calcium deposition was calculated from standard curves of known calcium concentrations run in parallel with experimental groups and normalized to control scaffolds which were digested to remove the contribution of embedded nano hydroxyapatite.

Total collagen content of lysed samples was evaluated via Sircol collagen assay kit (Accurate Chemical & Scientific Corp., Westbury, N.Y.). Per manufacturer instructions, 1 mL dye reagent was added to 100 μl lysate and shaken for 30 min. Samples were then centrifuged for 10 min at 10,000 rpm to pellet the collagen-dye complex and the supernatant was carefully decanted. Ice-cold wash reagent was used to remove unbound dye and the samples were centrifuged once more and the supernatant decanted. 250 μL alkali solution was added to solubilize the pellet and a 200 μl aliquot was transferred to a new 96-well plate and absorbance measurements were taken at 555 nm.

hMSC chondrogenic differentiation study: hMSCs were seeded at a density of 105 cells/scaffold. Seeded scaffolds were cultured in complete media supplemented with chondrogenic factors (100 nM dexamethasone, 40 μg/mL proline, 100 µg/mL sodium pyruvate, 50 µg/mL L-Asorbic acid 2-phosphate, and 1% (volume/volume) ITS+) for 1 and 2 weeks, respectively. At each prescribed time point, cell seeded samples were rinsed with PBS, lyophilized, then digested in a papain digestion solution for 18 h at 60° C. and stored at −80° C. until analyzed. Total collagen content of digested samples was evaluated as described previously.

Figure 4A:
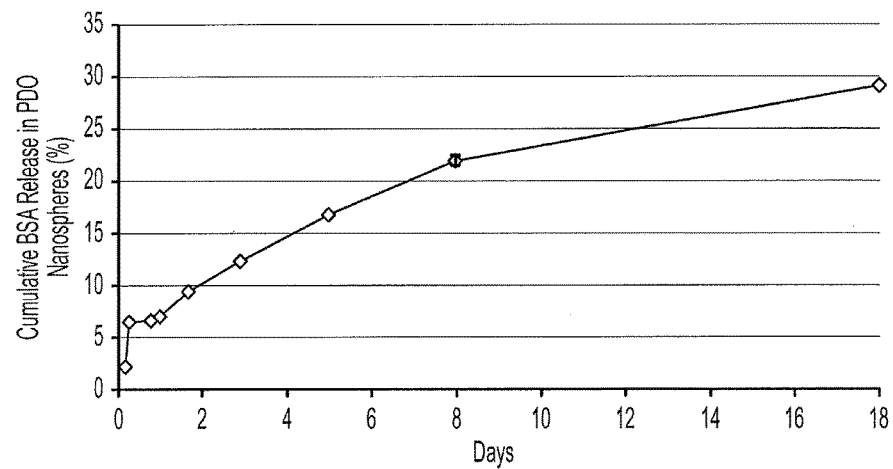
FIG. 4A shows the release profile of BSA encapsulated in PDO nanospheres.
Figure 4B:
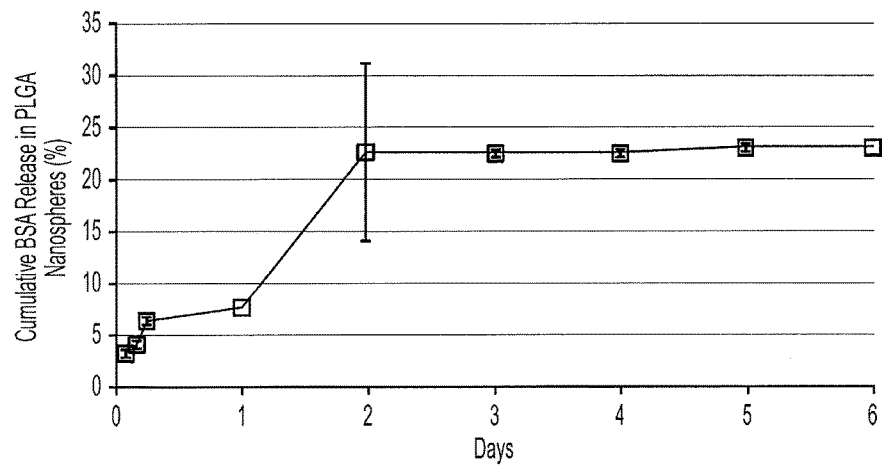
FIG. 4B shows the release profile of BSA encapsulated in PLGA nanospheres.

Glycosaminoglycan (GAG), a key component of cartilage matrix, was measured using a standard GAG assay kit (Accurate Chemical & Scientific Corp., Westbury, N.Y.) according to manufacturer's instructions. Briefly, a predetermined volume of sample and buffer solution was added to a microcentifuge tube with 500 µL of dye reagent and mixed for 30 minutes. The GAG-dye complex was centrifuged for 10 minutes at 10,000 g until a pellet was visible. The supernatant was decanted and all residual fluid was blotted of sustained delivery devices have been employed which include melt extrusion and thin film fabrication along with traditional emulsion techniques exhibiting encapsulation efficiencies of 26-62% for pure and copolymeric systems.[22-24] Encapsulation efficiencies as well as degradation rates can be readily modulated through the use of copolymeric systems as illustrated by de Boer et al[15] where 50:50 (lactic:glycolic acid) PLGA polymers yielded the greatest encapsulation as well as the smallest particle size. Release profiles of PDO/PLGA nanospheres as shown in FIGS. 4a and 4b, respectively, revealed a minimized burst release within the first 8 hours of incubation for both nanospheres and steady release to 18 days (PDO) and 6 days (PLGA), respectively. Hydrothermally-treated nHA particles (Figure A) have average dimensions of 50-100 nm in length and 20-30 nm6 wide similar to natural bone mineral.

TABLE 3

Swelling Properties of Cartilage Layer Samples
Characteristics of PEG:PEG-DA (60 wt %) hydrogels

|  | Control | Blank spheres | BSA-loaded spheres | TGF-β1-loaded spheres |
| --- | --- | --- | --- | --- |
| Swelling Ratio (%) | 279.76 ± 4.92 | 277.73 ± 4.60 | 277.63 ± 3.88 | 170.26 ± 10.11 |
| Sol Fraction (%) | 63.71 ± 0.39 | 63.27 ± 0.20 | 63.27 ± 0.20 | 64.26 ± 0.87 | dry. Next, 600 µL of dissociation reagent was added to the tubes and shaken for 30 minutes; 100 µL of each solution was placed into a 96-well plate and analyzed in triplicate. Absorbance was read at 656 nm and correlated to a standard curve of known standards.

Human Type II collagen was evaluated via a Type II collagen ELISA assay (Fisher Scientific, Pittsburgh, Pa.). Briefly, control and sample aliquots were added to a precoated 96-well plate and incubated. Unbound sample was washed and a horse radish peroxidase-labeled collagen II antibody was added, incubated, and washed. After washing, tetramethylbenzidine was added producing a blue color. The reaction was stopped by the addition of an acidic stop solution and read at 450 nm.

Statistical Analysis:

Data are presented as the mean value±standard error of the mean (StdEM) and were analyzed via one-way ANOVA and student's t-test to determine differences amongst the groups. Statistical significance was considered at p<0.05.

Results and Discussion

Figure 3A:
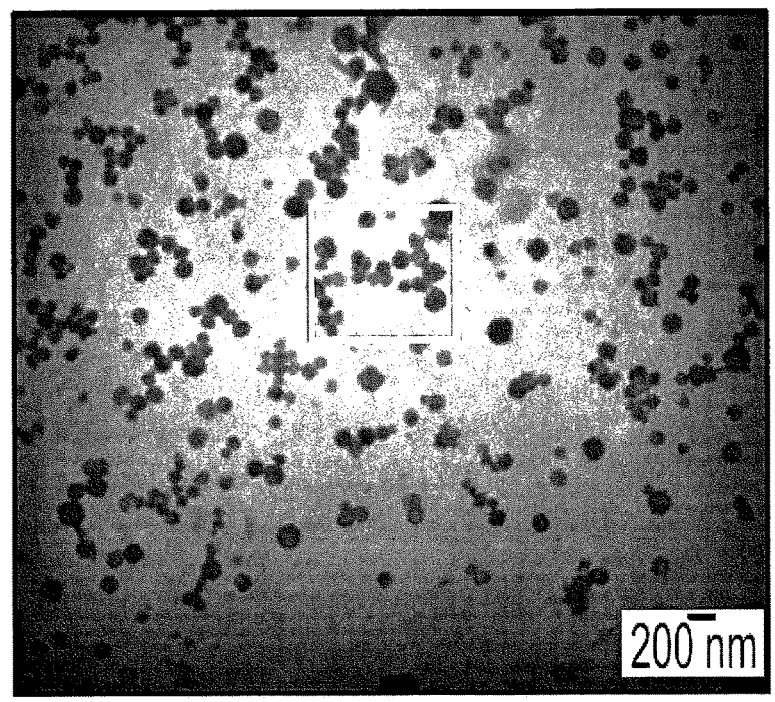
FIG. 3A shows TEM micrographs of BMP-2 encapsulated PDO nanospheres.
Figure 3B:
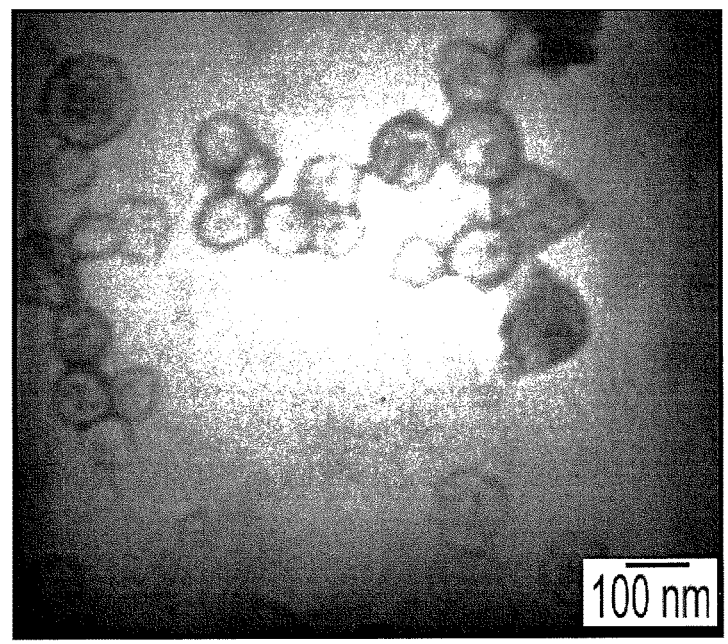
FIG. 3B shows a high magnification image of the highlighted area.
Figure 3C:
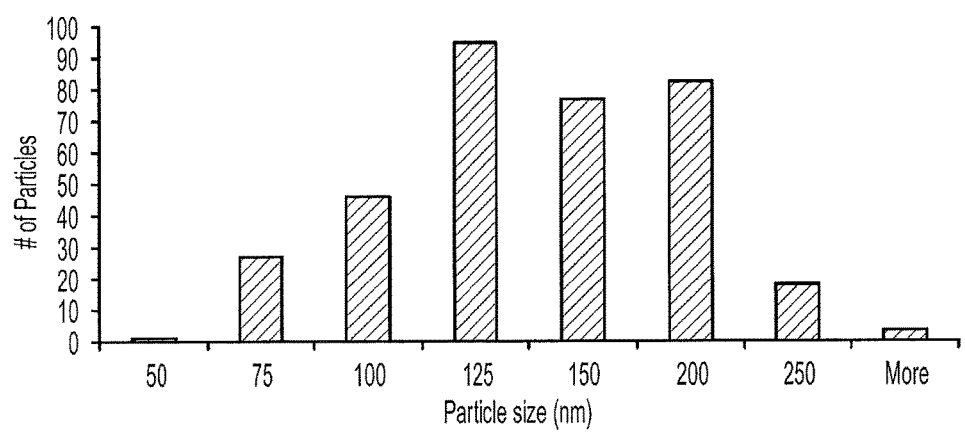
FIG. 3C shows a graph showing particle size distribution results of PDO nanospheres.

Nanomaterial Characterization:

TEM was employed to evaluate the morphology and particle size distribution of synthesized PDO/PLGA nanospheres. FIG. 3a shows TEM micrographs of BMP-2 encapsulated PDO nanospheres, and FIG. 3b shows a high magnification image of the highlighted area from FIG. 3a. Particle sizes ranged between 75 and 250 nm with an average particles size of 150 nm (FIG. 3c) with the core-shell morphology visible in FIG. 3b. Traditional emulsion-based micro-sphere or nano-sphere fabrication techniques have been extensively employed with limited control of particle size and encapsulation efficiency.[15-17] The wet electrospray method employed here allows for comparable or increased encapsulation efficiency of PDO (>70%) and PLGA (>80%), respectively, where traditional emulsion methods exhibit encapsulation efficiencies of 60-80% for PLGA.[15, −21] With respect to PDO, due to the material's relative insolubility, alternative methods for the fabrication PLGA and similar lactide and glycolide-based polymeric materials have been employed in the manufacture of controllable micro and nanospheres for drug delivery systems owing to the material's excellent biocompatibility, bioresorbability, and controllable degradation rates.[25-27] Degradation rates of PLGA constructs are governed by the ratio of each respective monomer within the polymeric backbone. 50:50 (lactide:glycolide) PLGA was used in the current studies which has been reported as having ~1-2 month degradation rate.[27] In addition, a hydrogel-based matrix allows for more exposure of embedded PLGA nanospheres within the construct due to the inherent swelling properties (Table 3) of the material as opposed to PDO nanospheres embedded within a PCL matrix. Currently, PDO, known commercially as PDS®, is commonly used as an absorbable suture.[28-30] Excellent biocompatibility, mechanical properties, as well as a slower degradation rate render it ideal for controlled drug delivery and tissue engineering applications.[31-35] Co-axial electrospraying[36] allows for easy fabrication of a novel controllable core-shell nanosphere with intact growth factors contained within a biodegradable polymer shell.

Figure 5A:
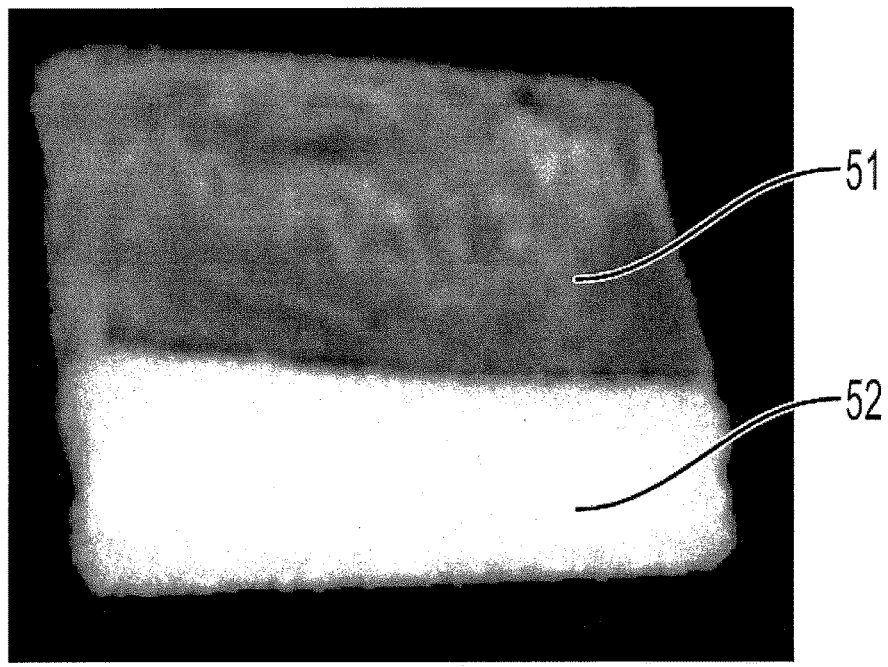
FIG. 5A shows an optical micrograph of biphasic biomimetic osteochondral nano scaffold.
Figure 5B:
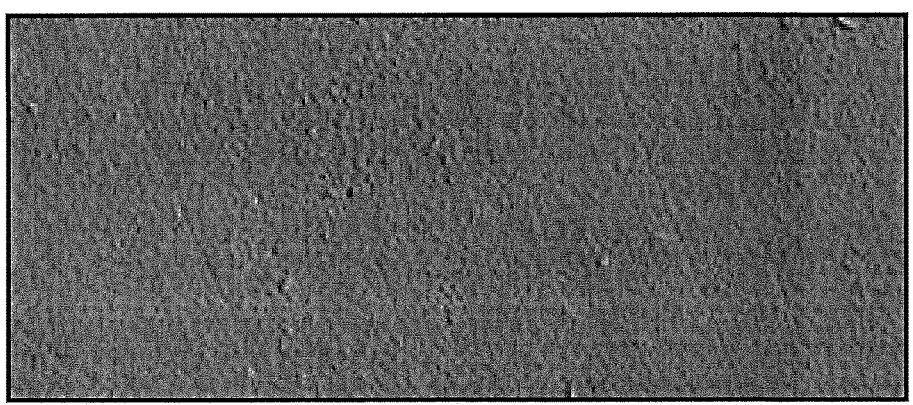
FIG. 5B shows an electron micrograph of the top layer of the scaffold.
Figure 5C:
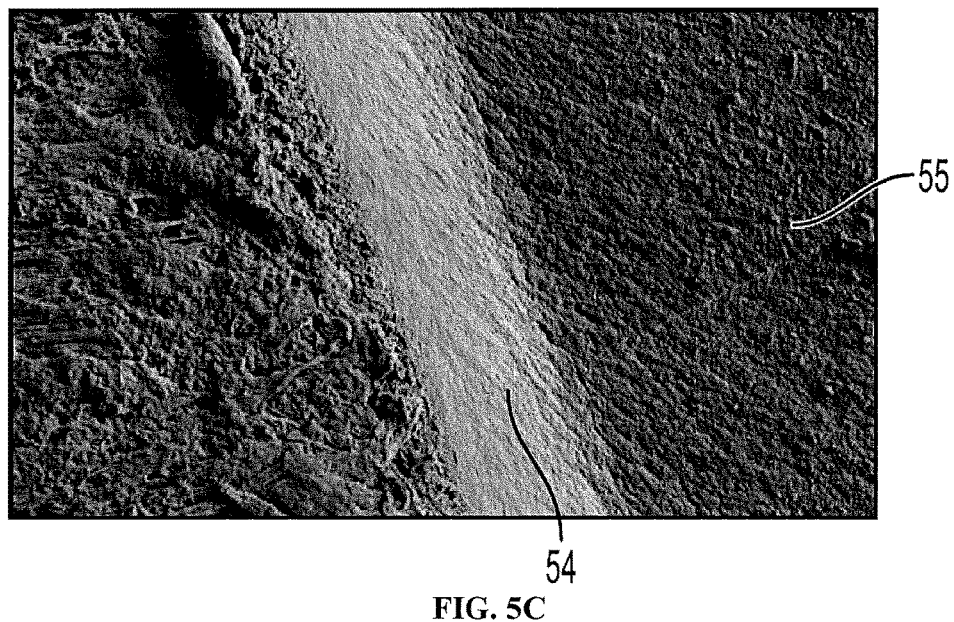
FIG. 5C shows an electron micrograph of the ultraviolet cross-linked surface.
Figure 5D:
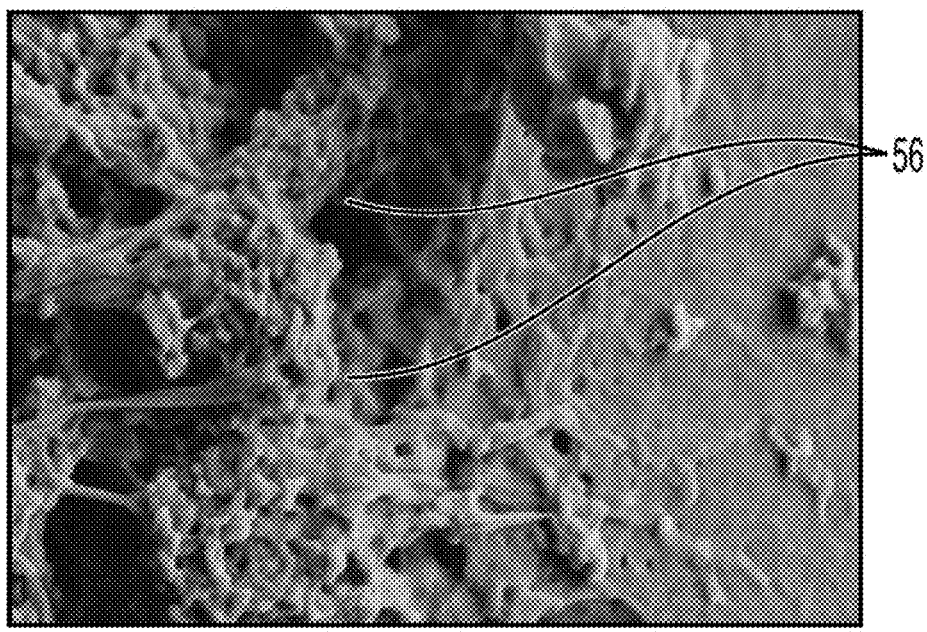
FIG. 5D shows a higher magnification of the interface region.
Figure 5E:
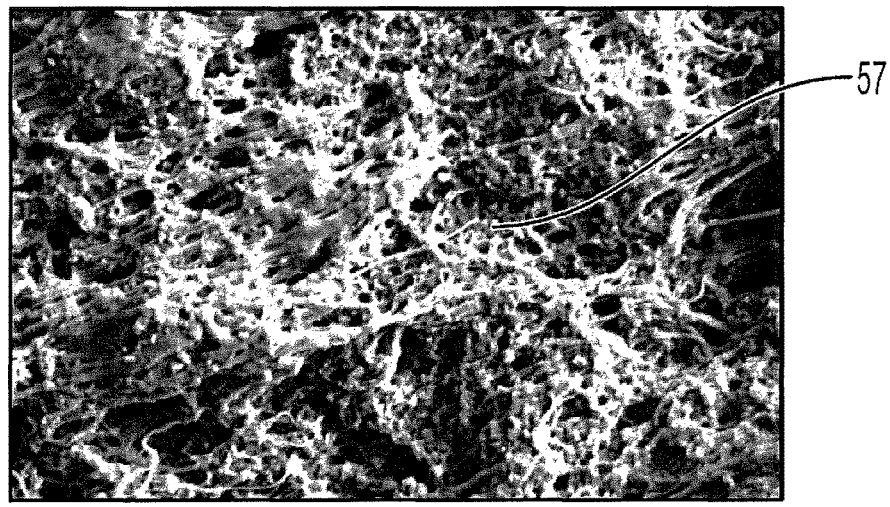
FIG. 5E shows an alternate view of a higher magnification of the interface region.
Figure 5F:
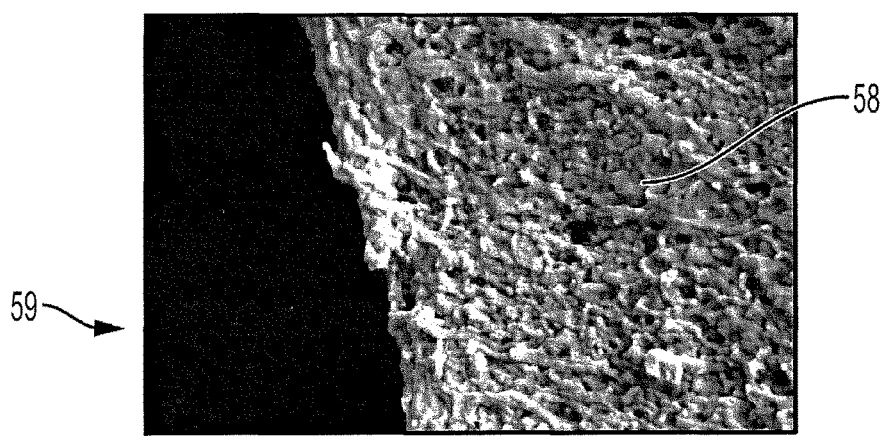
FIG. 5F shows the bone layer.
Figure 5G:
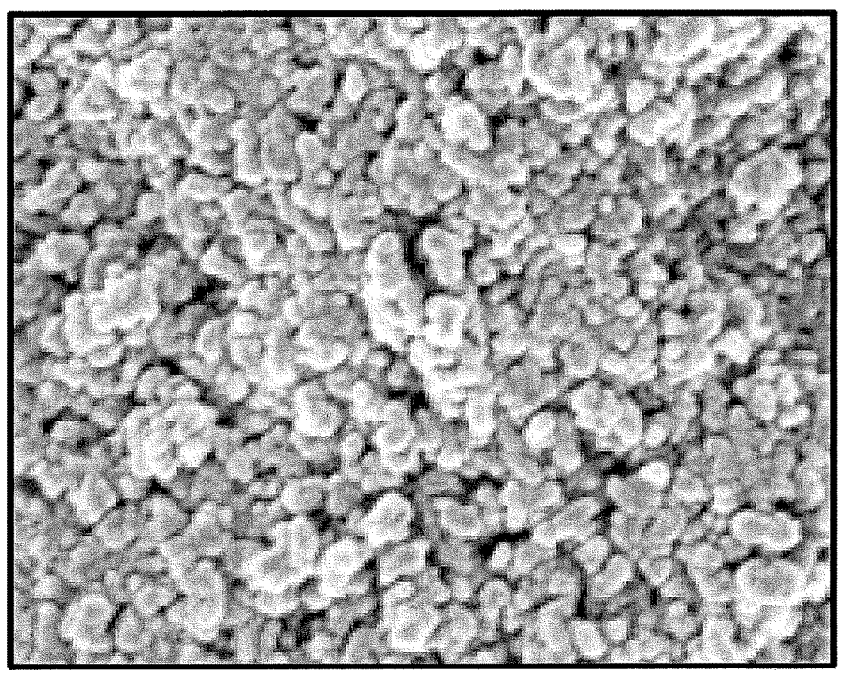
FIG. 5G shows hydrothermally-treated nHA particles.

Biphasic (PCL/PEG-Da) Osteochondral Scaffold Characterization and In Vitro hMSC Studies Optical and scanning electron micrographs (FIG. 5) of fabricated osteochondral scaffolds revealed excellent integration between the PEG-Da (cartilage) and PCL/PEG-Da (bone) layer. FIG. 5a shows an optical micrograph of the fabricated osteochondral scaffold and depicts the cartilage, 51, and bone, 52, layers. FIGS. 5b-5f are electron micrographs of the scaffold. FIG. 5b shows the top layer. FIG. 5c illustrates the UV crosslinked interface, 54, between the bone, 53, and cartilage, 55, layers. FIGS. 5d-5e show higher magnification of the interface region showing integration of nHA particles (56 and 57) into the bone layer. FIG. 5f shows the bone layer, 58, and bottom surface, 59. Due to the bulk crosslinking manufacturing technique employed here, a sharp transition between the respective layers was formed.

An interesting feature of the fabricated osteochondral scaffold is the formation of a fibrous nanostructured network formed orthogonally to the cured surface. In addition, due to the presence of the nHA nanoparticles within the bone layer, a more biomimetic scaffold has been developed with respect to morphology and composition.

Figure 6A:
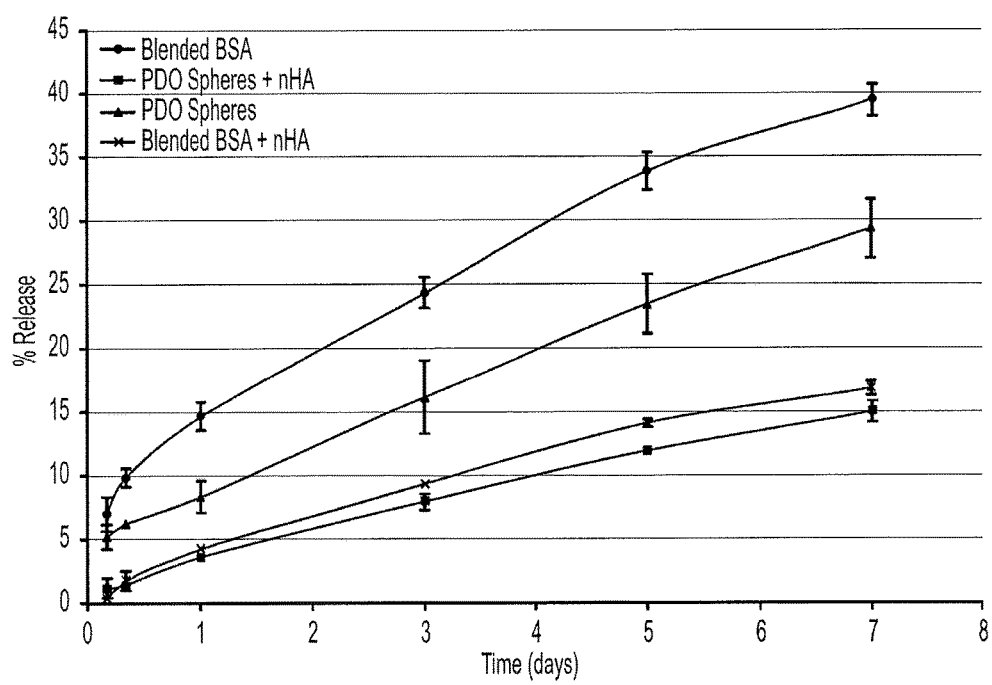
FIG. 6A shows release profiles of bone layer scaffolds with BSA encapsulated PDO nanospheres and blended BSA.
Figure 6B:
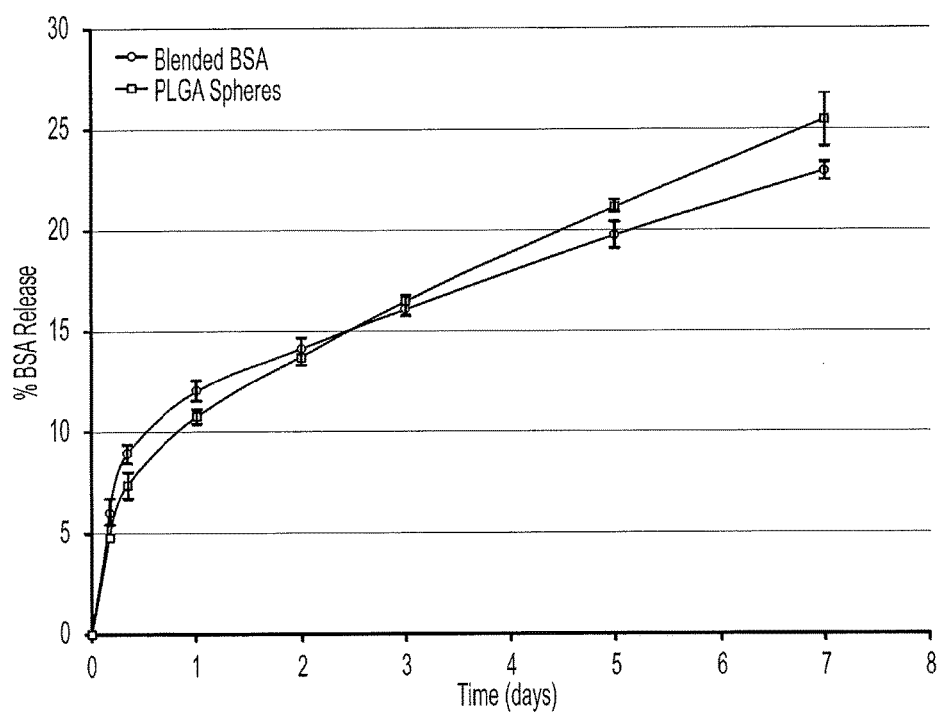
FIG. 6B shows release profiles of cartilage layer scaffolds with BSA encapsulated PLGA nanospheres and blended BSA.

Protein release studies of the respective tissue layers were investigated to determine the release kinetics of the nanocomposite system developed here. FIG. 6 shows the release profiles of blended and nanosphere encapsulated BSA for the respective tissue-specific layers. More specifically, FIG. 6 shows release profiles of bone layer scaffolds with BSA encapsulated PDO nanospheres and blended BSA (FIG. 6a), and cartilage layer scaffolds with BSA encapsulated PLGA nanospheres and blended BSA (FIG. 6b). Data are ±standard deviation, n=6. An interesting phenomenon was observed with regards to nHA-containing bone layer samples. A significant decrease in protein release was noted and is postulated to be attributed to electrostatic interactions between the negative carboxyl terminals of the globular protein and positively-charged species ($H+$ and $Ca2+$) of the nHA particles present at the material's surface as described by Tarafder et al. 37 Cartilage layer samples containing PLGA nanospheres exhibited similar release kinetics (FIG. 6b) when compared to pure nanospheres (FIG. 4b) with ~25% total protein released after 1 week of incubation.

Figure 7:
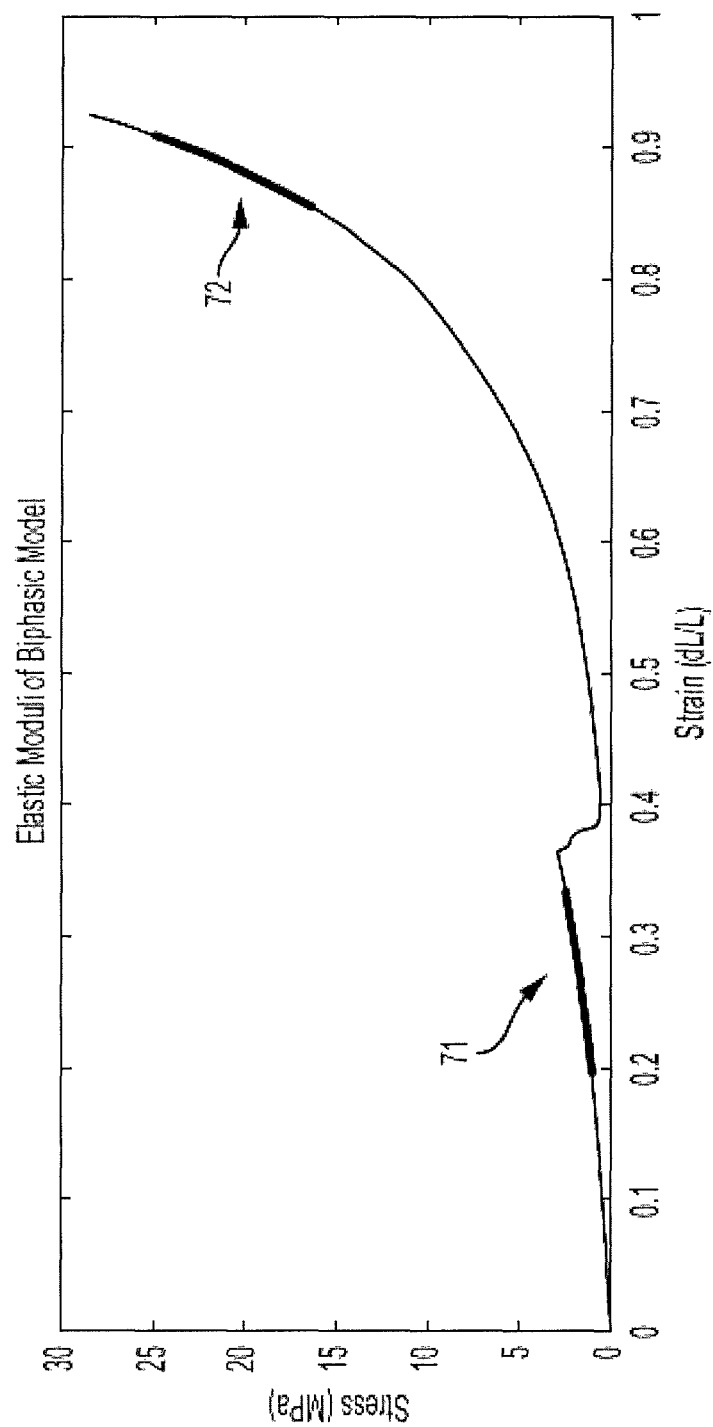
FIG. 7 shows a stress-strain curve of the biphasic nanocomposite osteochondral scaffold.

A representative stress-strain curve of fabricated biphasic nanocomposite scaffolds is illustrated in FIG. 7. The bimodal nature of the curve is reflective of the biphasic construct where region 71 (cartilage layer) ($R2=0.991$) and region 72 (bone layer) ($R=0.996$) exhibit elastic moduli of 6.07±0.170 MPa and 21.65±1.91 MPa, respectively. Due to the modular nature of the system, greater tunability of the mechanical properties can be achieved through the use of alternative photo cross-linkable hydrogels (ie. methacrylated PEG, poly(propylene) fumarate), as well as PEG derivatives of varying molecular weights. Both of the cartilage layer and bone layer compositions can be readily modified.

Figure 8:
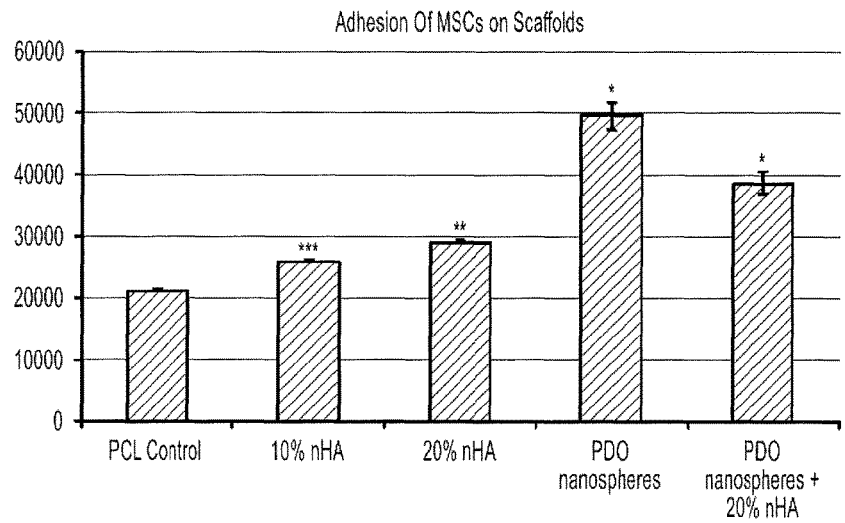
FIG. 8 shows enhanced hMSC adhesion on PCL scaffold with PDO nano-sphere and 20% nHA.

FIG. 8 shows the 4 hour cell adhesion study on bone layer scaffolds. The results show that cells attached more to 20% nHA than 10% or the 0% control. More importantly, the scaffolds containing PDO nanospheres and/or 20% nHA have the highest cell density, thus suggesting the very good cytocompatibility properties of the fabricated nanocomposite scaffolds. Data are mean±StdEM, n=9; *$p<0.05$ when compared to all other samples; $p<0.05$ when compared to 10% nHA in PCL and PCL controls; *$p<0.05$ when compared to PCL controls.

Figure 9:
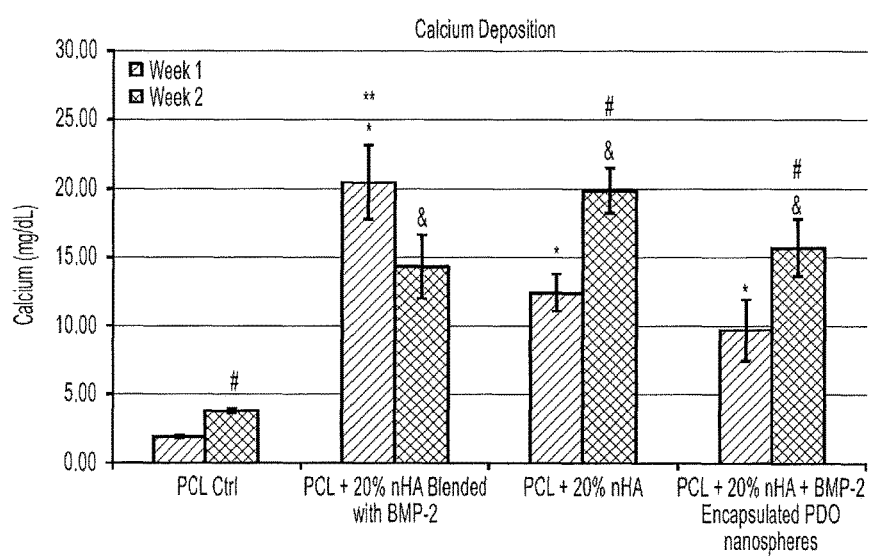
FIG. 9 shows calcium deposition of bone layer samples.

In the hMSC differentiation studies, the respective bone and cartilage layers of the osteochondral scaffold were evaluated for hMSC osteogenic and chondrogenic differentiation potential. Bone layer samples were evaluated for extracellular calcium deposition and total collagen production. The total calcium deposition (FIG. 9) revealed greater calcium deposition in all nanocomposite samples after 1 and 2 weeks. In addition, though blended BMP-2 into nHA scaffolds had a higher calcium deposition after 1 week, BMP-2 encapsulated nanospheres and nHA scaffolds showed a statistically significant increase from week 1 to week 2. Data are mean±StdEM, n=6; **$p<0.01$ when compared to all samples and *$p<0.01$ when compared to controls after 1 week of culture. &$p<0.01$ when compared to controls after 2 week of culture and #$p<0.05$ when compared to respective scaffold in week 1.

Figure 10:
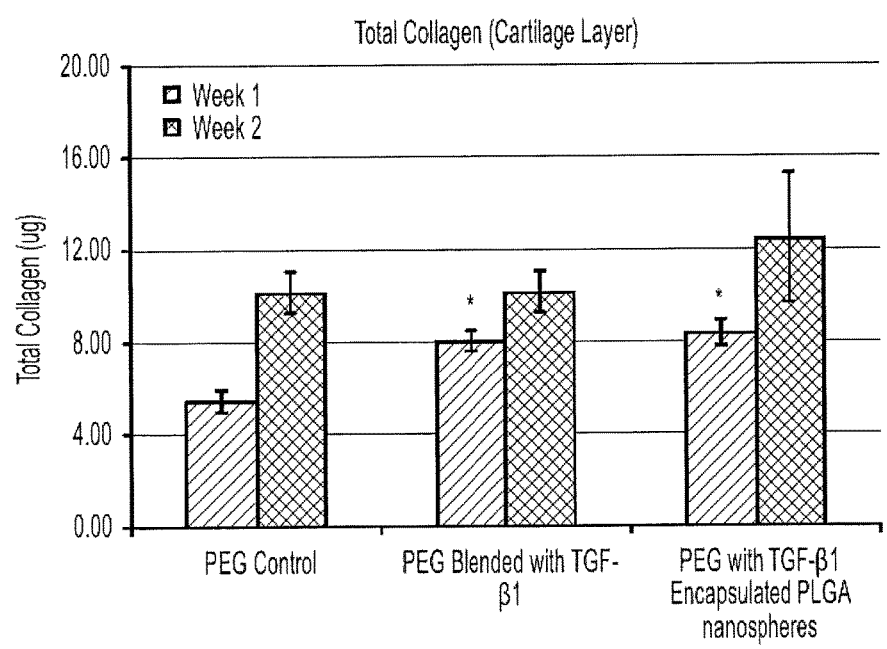
FIG. 10 shows significantly improved total collagen content in nanocomposite bone layer scaffolds after 2 week of culture.

Total collagen synthesis (FIG. 10) increased in all nanostructured bone layer samples with respect to control after 2 weeks of culture. Although no distinguishable difference was observed after 1 week, after 2 weeks all nHA/BMP-2 PCL samples performed better than PCL control samples, as well as showed a statistically significant increase in collagen production when compared to week 1. Moreover, our results show that BMP-2 encapsulated PDO nanospheres can achieve the highest collagen synthesis when compared to BMP-2 blended and all other samples after 2 weeks. Although various growth factors (e.g., TGF-β1 and BMP-2) have been shown to improve MSC osteogenic or chondrogenic differentiation,[38-48] methods for administering them face ongoing issues with regards to short-term retention, quick half-life in circulation, and quick loss of biological activity even when administered at high dose rates. When local delivery to the osteochondral defect site is employed, rapid diffusion to adjacent tissues and loss of bioactivity limits their potential to promote prolonged osteochondral tissue formation in the defect site. In our study, we designed a series of novel PDO nanospheres which can release BMP-2 in a sustained and controlled fashion, thus potentially facilitating long-term tissue regeneration. Our osteogenic differentiation study has demonstrated that our nanostructured bone layer scaffold with nHA and BMP-2 encapsulated PDO nanospheres are promising for osteochondral tissue regeneration applications. Data are mean±StdEM, n=6; *$p<0.01$ when compared to PCL control after 2 week and **$p<0.05$ when compared to respective scaffolds in week 1. Nano-sphere containing samples also showed greater collagen content with respect to BMP-2 blended samples (&$p<0.05$).

Figure 11:
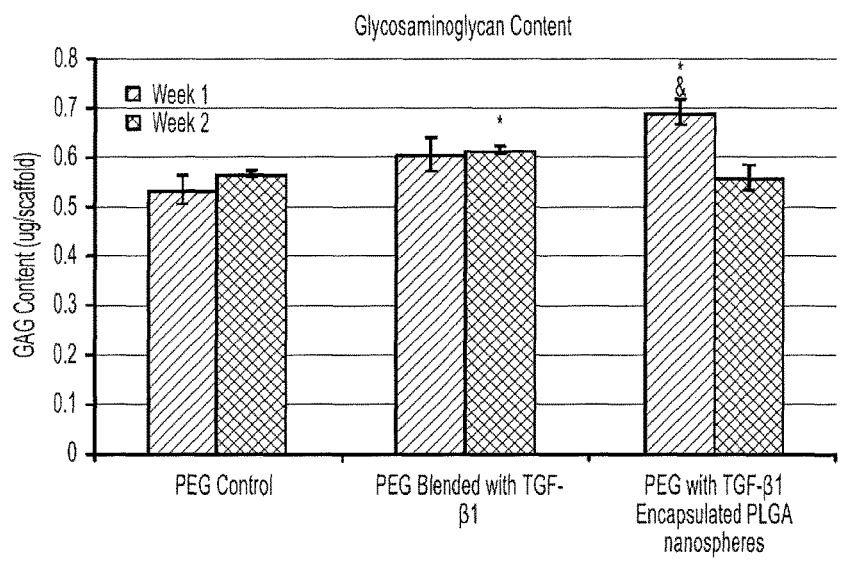
FIG. 11 shows total GAG content of cartilage layer samples.
Figure 12:
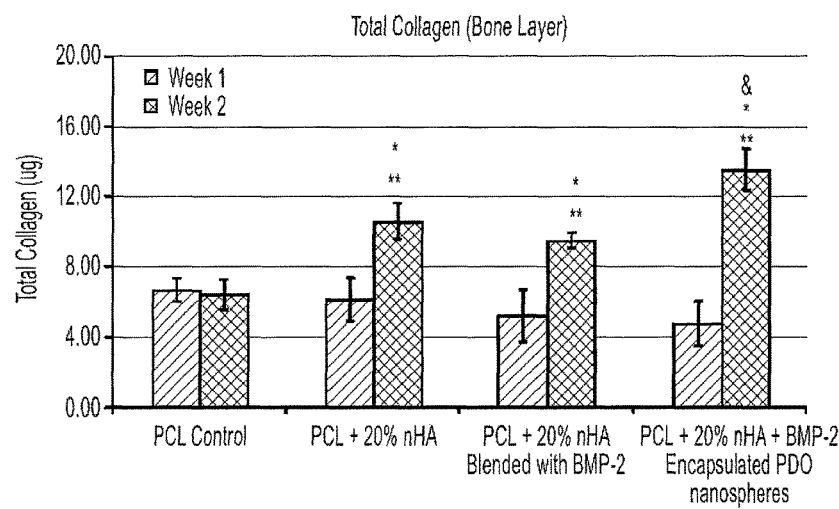
FIG. 12 shows total collagen content of cartilage layer samples.
Figure 13:
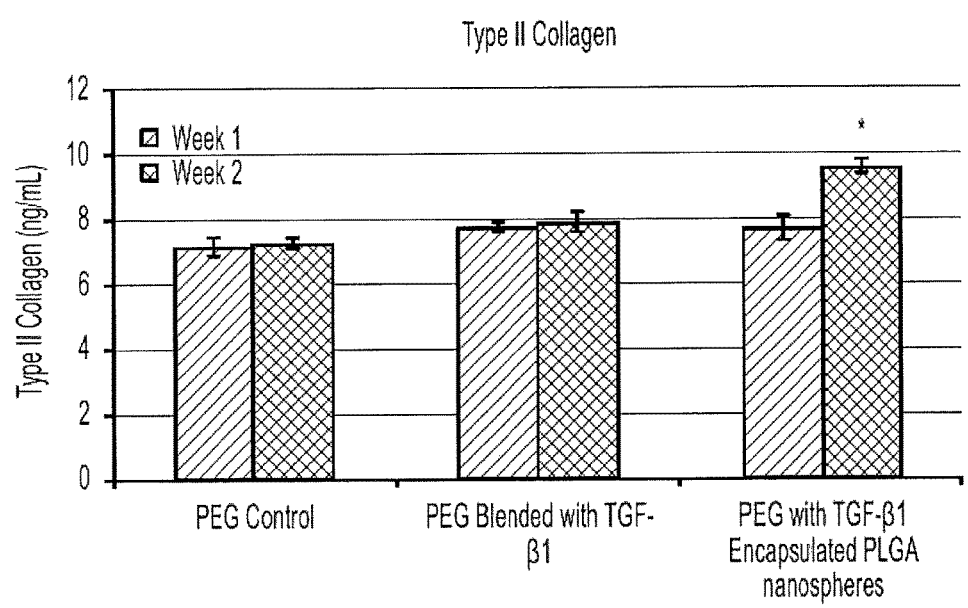
FIG. 13 shows type II collagen content of cartilage layer samples.

Biochemical analysis of 1 and 2 week chondrogenic hMSC differentiation showed PLGA nano-sphere scaffolds with encapsulated TGF-β1 performed better than untreated control (FIGS. 11-13). Specifically, there was a significant increase in GAG content after 1 week (FIG. 11). TGF-β1 has been shown to positively direct early and late-stage hMSC chondrogenic differentiation from initial increased GAG production to hypertrophic maturation of seeded hMSCs. Tezcan et al[49] examined TGF-β1 induced MSC chondrogenic differentiation and correlated their findings as a dose-dependent response wherein TGF-β1 was critical in the initiation of GAG synthesis and late stage hypertrophy and maturation. The decrease in GAG synthesis on PLGA nano-sphere cartilage samples may be attributed to this dose-dependent relation. Data are mean±StdEM, n=6; &$p<0.01$ when compared to week 1 control; *$p<0.05$ when compared to week 2 sample; +$p<0.05$ when compared to all week 2 samples.

FIG. 12 illustrates the total collagen synthesis in cartilage layer scaffolds. No statistical difference was observed among the experimental groups after 2 weeks. However, it was observed that both TGF-β1 containing samples had increased collagen synthesis when compared to control after 1 week of culture, which aided in promoting early cartilage formation. Data are mean±StdEM, n=6; Both blended and nanosphere encapsulated TGF-β1 samples out performed control after 1 week (*$p<0.01$). More importantly, type II collagen is a late-stage marker of chondrogenic differentiation which significantly increased after 2 weeks (FIG. 13) for PLGA nanosphere scaffolds when compared to control and TGF-β1 blended scaffolds. Data are mean±StdEM, n=6; nanosphere encapsulated TGF-β1 samples out performed control after 1 week (*$p<0.05$). All of these data reveal the great potential of novel TGF-β1 encapsulated PLGA nanosphere hydrogel scaffolds in improving chondrogenic differentiation of hMSCs.

Conclusions

The work presented herein served to illustrate the feasibility of manufacturing a novel biphasic osteochondral nanocomposite scaffold with controlled growth factor release. It differs from recently published work in the field wherein the current work focused on modulating hMSC behavior via a biomimetic scaffold composed of biocompatible polymeric materials and bioactive nanobiomaterials. Novel aspects of the current study include the development of an efficient wet electrospray technique to manufacture growth factor encapsulated core-shell nanospheres in addition to co-porogen UV crosslinking of two disparate polymeric materials. hMSC adhesion and osteochondral differentiation were enhanced through the incorporation of tissue-specific nanomaterials including nHA, BMP-2-loaded PDO and TGF-β1-loaded PLGA nanospheres. Due to the nature of the model, additional growth factor encapsulated spheres can be readily incorporated and evaluated for neovascularization. The current biphasic osteochondral model and nanosphere fabrication method hold great potential for orthopedic tissue engineering applications.

Example 2: Integrating Biologically Inspired Nanomaterials and Table-Top Stereolithography for 3D Printed Biomimetic Osteochondral Scaffolds The osteochondral interface of an arthritic joint is notoriously difficult to regenerate due to its extremely poor regenerative capacity and complex stratified architecture. Native osteochondral tissue extracellular matrix is composed of numerous nanoscale organic and inorganic constituents. Although various tissue engineering strategies exist in addressing osteochondral defects, limitations persist with regards to tissue scaffolding which exhibit biomimetic cues at the nano to micro scale. In an effort to address this, the current work focused on 3D printing biomimetic nanocomposite scaffolds for improved osteochondral tissue regeneration. For this purpose, two biologically-inspired nanomaterials have been synthesized consisting of (1) osteoconductive nanocrystalline hydroxyapatite (nHA) (primary inorganic component of bone) and (2) core-shell poly(lactic-co-glycolic) acid (PLGA) nanospheres encapsulated with chondrogenic transforming growth-factor β1 (TGF-β1) for sustained delivery. Then, a novel table-top stereolithography 3D printer and the nano-ink (i.e., nHA+nanosphere+hydrogel) were employed to fabricate a porous and highly interconnected osteochondral scaffold with hierarchical nano-to-micro structure and spatiotemporal bioactive factor gradients. Our results showed that human bone marrow-derived mesenchymal stem cell adhesion, proliferation, and osteochondral differentiation were greatly improved in the biomimetic graded 3D printed osteochondral construct in vitro. The current work served to illustrate the efficacy of the nano-ink and current 3D printing technology for efficient fabrication of a novel nanocomposite hydrogel scaffold. In addition, tissue-specific growth factors illustrated a synergistic effect leading to increased cell adhesion and directed stem cell differentiation.

Recent advancements in the area of tissue engineering and the development of porous three-dimensional (3D) implantable scaffolds for tissue regeneration have placed a greater demand on the need for novel biomaterials which exhibit bioactive properties, as well as lend themselves to be tunable and modifiable for tissue-specific applications. Traditional methodologies such as porogen leaching[51-53] and gas foaming[54, 55] have been extensively studied and employed in the fabrication of porous scaffolds, but several limitations exist; namely, the lack of control of uniform pore dispersion, pore geometry, pore size, and interconnectivity,[56-59] all of which are necessary for successful integration of the 3D scaffold and host tissue.[60-62] More advanced scaffold fabrication techniques such as the twin-screw extrusion system used by Erisken et al.[63-65], Ozkan et al.[66, 67], and Ergun et al.[68, 69] have addressed some of these limitations while also focusing on spatially controlled incorporation of tissue-specific morphogenetic factors for enhanced and directed cell behavior. Another strategy which has been applied towards this research area is 3D bioprinting.

3D bioprinting technologies provide a promising means of addressing the aforementioned limitations of traditional scaffold fabrication methods by allowing for precise control and placement of biomaterials, cells, and bioactive factors within a pre-designed natural or synthetic 3D tissue matrix.[70, 71] With the development of novel biomaterials tailored to a specific 3D printing technology, tissue-specific 3D scaffolds with desirable chemical and mechanical properties can be readily manufactured. One such 3D printing technology which has garnered greater attention for use in the manufacture of bioactive 3D scaffolds is stereolithography (SL).[72, 73] SL can be used to manufacture 3D scaffolds for tissue regeneration applications due its capability of producing highly accurate 3D parts. The 3D scaffold can be created by polymerizing and/or photocrosslinking a liquid resin via ultraviolet (UV) light resulting in solidification of the liquid resin in a layer-by-layer process yielding a pre-designed 3D architecture. SL printing has shown the capacity of higher resolution, more accuracy, and precise control of 3D internal and external architecture than many other techniques. Unfortunately, constraints related to costs and maintenance of commercial systems have limited their wide access to research laboratories. Therefore, one aim of the current work was to develop a table-top stereolithography system capable of resolving features akin to industrial systems for the fabrication of multi-material bioactive scaffolds for osteochondral regeneration.

In addition to manufacturing constraints, a dearth of 3D printable bioinks with biomimetic nanoscale features for SL and other 3D bioprinting systems exists. An ideal bioink for 3D bioprinting should satisfy several essential criteria. Firstly, it should be biocompatible, bioactive and biomimetic for maximal cell growth and tissue integration. Secondly, they should be employable within various 3D bioprinting platforms. Unfortunately, only few available synthetic and natural biomaterials have shown to be suitable for 3D bioprinting to include: poly(ethylene glycol) (PEG) and derivatives, collagen, hyaluronic acid, and others.[74, 75] It is still particularly challenging to fabricate highly biomimetic tissue constructs based on current available biomaterials while regulating transplanted or native cell population(s) for efficient tissue regeneration. In fact, the native osteochondral extracellular matrix (ECM), is structurally hierarchical and nanocomposite in nature.[1] Nanobiomaterials, a research area at the forefront of nanotechnology and biomaterials, are designed to resemble cellular microenvironment components and regulate cell behavior, which are currently having a profound impact on the field of tissue regeneration.[1] However, current nanobiomaterials for 3D bioprinting of functional osteochondral tissue are extremely limited.[70]

Therefore, the main objective of this study is to develop biologically-inspired nanomaterials to be used as a series of bioinks for the fabrication of biomimetic graded osteochondral scaffolds via a novel table-top SL system. Two bioactive nanomaterials were synthesized in this study: one is hydrothermally treated nanocrystalline hydroxyapatite (nHA)[76-80]

which can not only serve as a nano mechanical reinforcer, but also as an osteoconductive factor due to its biomimetic structure and composition. The other nanomaterial is a core-shell poly(lactic-co-glycolic) acid (PLGA) nanosphere encapsulated with chondrogenic transforming growth-factor β1 (TGF-β1) via a coaxial electrospraying technique. The core-shell nanospheres aim to serve as a sustained growth factor delivery system for sustained TGF-β1 delivery. The selected PLGA has excellent biocompatibility, mechanical properties, and a slower degradation rate, rendering it ideal for controlled growth factor delivery. Coaxial electrospraying[81] enables the separation of organic and aqueous phases and thus allows for effective incorporation of biologically active components such as growth factors into the aqueous phase with no exposure to harmful organic solvents.

Figure 14:
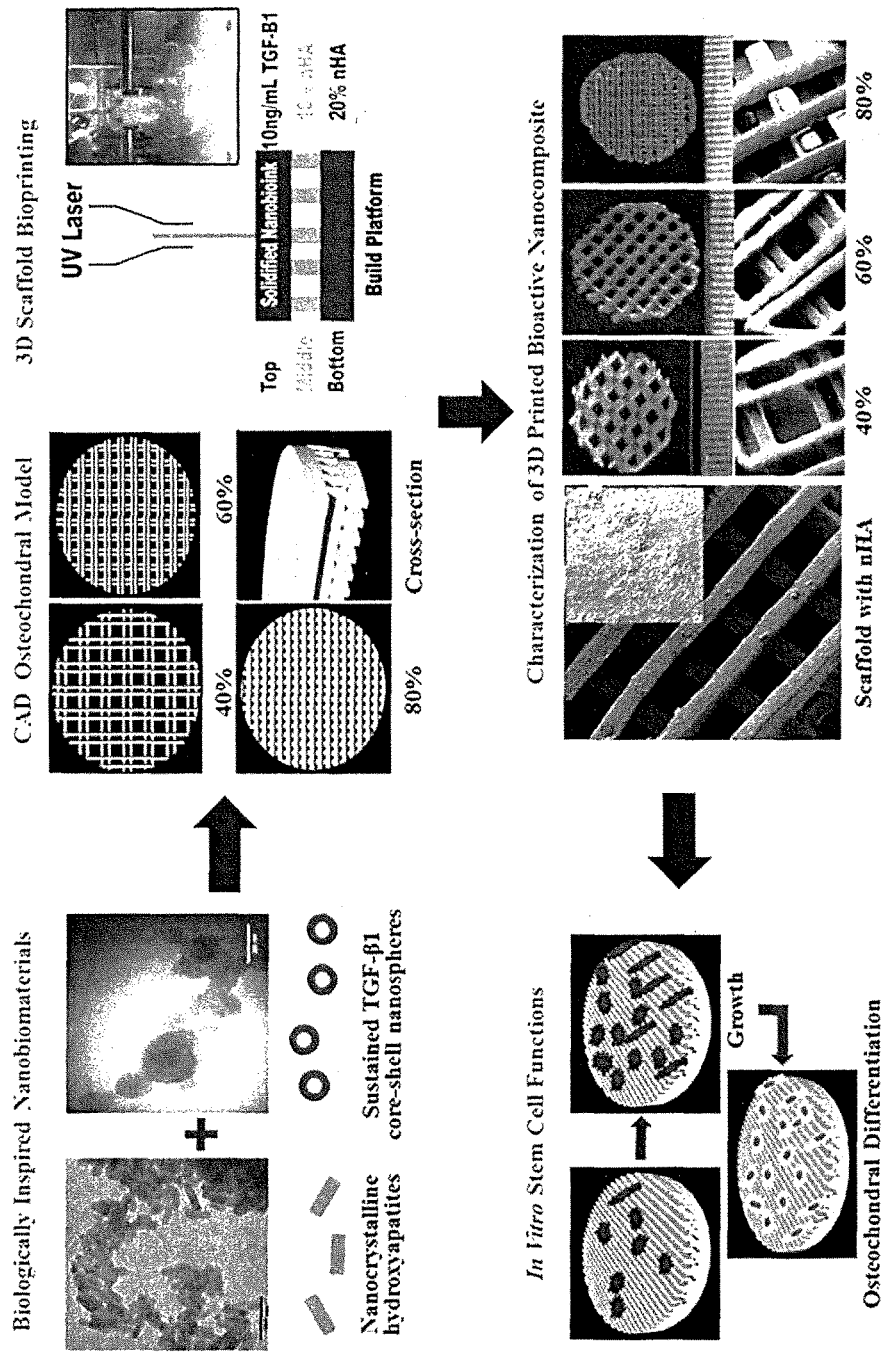
FIG. 14 shows a flow chart of SL printed biomimetic nanocomposite osteochondral scaffold.

FIG. 14 shows the overall design of the study. FIG. 14 shows a flow chart of SL printed biomimetic nanocomposite osteochondral scaffold. Tissue-specific nanomaterials for osteogenic (nHA) and chondrogenic (TGF-β1 loaded PLGA nanospheres) differentiation of hMSCs. CAD model of porous scaffold design and composition. 3D printed bioactive scaffolds via table-top SL and in vitro hMSC studies.

With the use of computer-aided design (CAD) software and table-top SL printing, bioactive biomimetic scaffolds containing graded osteochondral scaffolds were fabricated with nHA within the highly porous subchondral bone layer and chondrogenic TGF-β1 nanospheres in the cartilage layer for enhanced osteochondral regeneration. The following experimental groups were tested: a three layer scaffold (2 bone layers/1 cartilage layer) (−nHA/−TGF-β1) served as a control alongside the following experimental groups "graded" (+20% and 10% nHA/−TGF-β1), "blended" (+20% and 10% nHA/+bare TGF-β1), and "spheres" (+20% and 10% nHA/+TGF-β1 nanospheres). The effectiveness of incorporating spatiotemporal nanomaterials and growth factor cues for directed human bone marrow derived mesenchymal stem cell (hMSC) adhesion, growth, chondrogenic and osteogenic differentiation was explored in vitro. The proposed work also illustrates the capacity of our table-top SL printer in fabricating physiologically relevant nanocomposite scaffolds.

EXPERIMENTAL

Development of a Table-Top SL Printer

Printer design and cure depth assessment: The novel table top SL apparatus was developed based on the existing Solidoodle® 3D printer platform for use as a desktop SL system for additive manufacturing of nanomaterials. Open source software (Prontrface®) was employed to control the 3 stepper motors with an effective resolution of 100 μm in x, y, and z-axis. The major modification to the existing platform is the incorporation of a 110 μm fiber optic-coupled solid-state UV (355 nm) laser (MarketTech, Scotts Valley, Calif.). Per the manufacturer's specifications, the effective spot size of the emitted light is 190±50 μm with an energy output of ~20 uJ at 15 kHz. A glass petri dish was fixed upon the print bed to function as a minivat for the addition of liquid photocurable resin. Due to the ability to alter the frequency of the pulsed signal, power at the material's surface can be controlled with a range ~40-110 mW.

A 60% wt/wt polyethylene glycol diacrylate (PEG-Da, Mn=700) in PEG (Mw=300) hydrogel solution was selected as a bulk printing matrix material to characterize cure depth of the printer and used for the incorporation of tissue-specific nanomaterials in all studies. A photoinitiator, Bis(2, 4,6-trimethylbenzoyl)-phenylphosphineoxide (BAPO) (BASF, Florham Park, N.J.), with excitation in the ultraviolet (UV) range was added to the PEG:PEG-Da mixture at 0.5 wt % of PEG-Da and allowed to rest overnight for adequate dissolution. Specifically, the hydrogel solution was pipetted inside a plastic petri dish filled up to the rim. A glass slide was placed on top of the container, in contact with the solution. The glass slide acted as a substrate that allowed the gel to adhere to the underside of the glass slide during laser exposure thus facilitating the measurement of the solidified gel. Samples were cured by activating the laser and drawing a line at various print speeds through the glass slide and into the PEG-Da photopolymer solution. After polymerization, the glass slide was lifted off the petri dish containing the adhered polymerized gel. The cured gels were rinsed with distilled water to remove unreacted PEG-Da, and the thickness (in z) of the gels was then measured with a micrometer. Five gels were cured for each of the PEG-Da solutions, and the average thickness was determined.

Hydrothermally Treated nHA and TGF-β1 Encapsulated PLGA Core-Shell Nanospheres Synthesis nHA synthesis: A wet chemistry plus hydrothermal treatment method was used to synthesize nHA with good crystallinity and nanometer particle size as described in our previous papers[3, 4, 11, 82, 83]. Briefly, 37.5 mL of a 0.6 M ammonium phosphate (Sigma Aldrich, St. Louis, Mo.) solution was added to 375 mL of water and adjusted to pH 10 with ammonium hydroxide (Fisher Scientific, Pittsburgh, Pa.). A 1 M calcium nitrate (Sigma Aldrich, St. Louis, Mo.) solution added dropwise into the above mixture while stirring. Precipitation of HA continued for 10 min at room temperature. Upon complete addition of calcium nitrate, the HA precipitate containing solution was hydrothermally treated at 200° C. for 20 h in a 125 mL Teflon liner (Parr Instrument Company, Moline, Ill.). After 20 h, the nHA precipitate was centrifuged and rinsed thoroughly with water three times, dried at 80° C. for 12 h and ground into a fine powder.

TGF-β1 encapsulated core-shell nanosphere fabrication: Poly(lactic-co-glycolic) acid (PLGA) (Lactel Absorbable Polymers, Birmingham, Ala.) nanospheres were fabricated by coaxial wet electrospray via a custom coaxial needle system. The coaxial system consisted of a 26 G core needle (304SS 0.018" OD, 0.01"ID) receded within a 20G shell needle (304SS 0.036" OD, 0.0275" ID) (McMaster-Carr, Robbinsville, N.J. 08691). Specifically, TGF-β1 (Pepro-Tech, Rocky Hill, N.J.) lyophilized powder was resuspended per manufacturer's instructions (10 ng/mL) and used in all experiments. For TGF-β1 encapsulated nanospheres, a 2.5% (weight %) solution of PLGA in acetone (Sigma-Aldrich, St. Louis, Mo.) was fed through the shell feed inlet at a flow rate of 4.0 mL/hour. TGF-β1 was fed through the core feed inlet at the same flow rate. Voltage was adjusted during collection to prevent fiber formation and maintain adequate Taylor cone morphology. PLGA nanospheres were collected in an ultrapure water stabilizing bath. After collection, the bath was transferred to a centrifuge tube and ultrasonicated for 30 seconds (Ultrasonicator, QSonica, Newtown, Conn.). Emulsified samples were then immediately frozen and lyophilized for 24 hours to remove the stabilizing bath prior to use. Transmission electron microscopy (TEM, JEOL 1200 EX) was employed for morphological examination and size analysis of the two synthesized nanomaterials.

Bioactive Graded Osteochondral Scaffold Fabrication 3D scaffold design and printing: A series of 15 mm×1.2 mm solid disks with predesigned architecture were designed in Rhinoceros3D (McNeel North America, Seattle, Wash.), prepared for 3D printing using the open source software package Slic3r, and fabricated via our table-top SL printer. The previously characterized PEG-Da:PEG mixture was used for all experiments. Specifically, 3 mL of the hydrogel solution was added to a rigid glass petri dish fixed upon the print bed and allowed to dwell for 2 minutes. The volume used produced an effective layer thickness of 400 μm. For hMSC adhesion and proliferation studies, bare hydrogel scaffolds with increasing in-fill density (40%, 60%, and 80%) which corresponds to the solid fraction of each printed layer were fabricated. Then, graded osteochondral scaffolds were fabricated with nHA concentrations of 20% and 10% weight % of PEG-Da for the porous osseous layer and transitional calcified cartilage layer with a solid cartilage layer containing either bare TGF-β1 (10 ng/mL) or TGF-β1 encapsulated nanospheres of equivalent concentration for enhanced chondrogenesis. Fabricated samples were rinsed in ultrapure water and allowed to swell overnight for dissolution of the soluble PEG fraction. Upon swelling, a 5 mm biopsy punch was used to collect cylindrical samples. Scaffold morphology was examined via scanning electron microscopy (SEM, Zeiss NVision 40 FIB) at 3 kV accelerating voltage.

TGF-β1 release study: Two week TGF-β1 release profiles in the scaffolds containing bare TGF-β1 or TGF-β1 encapsulated nanospheres were evaluated. Briefly, 5 mm of the above two types of scaffolds (n=3) were incubated in phosphate-buffered saline (PBS) at 37° C. Fractions of the supernatant were collected after 4, 24, 72 hours, 1 and 2 weeks, respectively and TGF-β1 content was measured spectrophotometrically (Multiskan GO® Spectrophotometer, Thermo Scientific, Waltham, Mass.) via a TGF-β1 enzyme-linked immunosorbent assay (ELISA). Growth factor release profiles were plotted as a fraction of total encapsulated growth factor.

Mechanical testing: The compressive elastic modulus of the 3D printed scaffolds was determined via uniform compression testing (n=5) (Applied Test Systems, Butler, Pa.) fitted with a 100 N load cell at a crosshead speed of 5 mm/min. 5 mm samples were placed in ultrapure water and allowed to swell for 24 hours with intermittent exchange of fresh ultrapure water and blotted dry prior to testing. Load and displacement were used to plot the stress-strain curves and the Young's modulus was calculated from the linear elastic region.

hMSC In Vitro Studies

Primary hMSCs were obtained from healthy consenting donors from the Texas A&M Health Science Center, Institute for Regenerative Medicine. The cells (passage #3-6) were cultured in complete media composed of Alpha Minimum Essential medium (α-MEM, Gibco, Grand Island, N.Y.) supplemented with 16.5% fetal bovine serum (Atlanta Biologicals, Lawrenceville, Ga.), 1% (v/v) L-Glutamine (Invitrogen, Carlsbad, Calif.), and 1% penicillin:streptomycin (Invitrogen, Carlsbad, Calif.) and cultured under standard cell culture conditions (37° C., a humidified, 5% CO2/95% air environment). All 3D printed samples were sterilized in 70% ethanol for 30 min then washed 3 times for 5 min in PBS before cell seeding.

hMSC adhesion and proliferation: Porous multilayer scaffolds of increasing in-fill density were evaluated for hMSC adhesion. Specifically, hMSCs were seeded at 50,000 cells/scaffold. Seeded scaffolds were incubated under standard cell culture conditions for 4 hours. After rinsing with PBS, the adherent cells were lifted enzymatically and quantified via MTS assay (CellTiter 96® AQueous Non-Radioactive Cell Proliferation, Promega, Madison, Wis.) and analyzed at 490 nm. Similarly, hMSC proliferation was examined on graded bioactive scaffolds with nHA concentrations of 20% and 10% wt % of PEG-Da. hMSCs were seeded at 10,000 cells/scaffold and incubated for 1, 3, and 5 days under standard stem cell culture conditions. After rinsing with PBS, the adherent cells were quantified via the MTS assay as previously described.

Confocal microscopy: hMSC 3 and 5 day growth morphology were examined on control and SL printed graded nHA scaffolds. hMSCs were seeded at a density of 50,000 cells and cultured for 3 and 5 days, respectively. The scaffolds were rinsed with PBS 3 times followed by fixation with 4% formaldehyde for 20 min and double-stained with DAPI (cell nucleus) and Texas-Red (actin cytoskeleton), respectively. A ZIESS 710 laser scanning confocal microscope was employed to visualize stem cell spreading morphology.

hMSC chondrogenic and osteogenic differentiation: hMSCs were seeded at a density of 105 cells/scaffold for hMSC differentiation. A multilayer scaffold in the absence of morphogenic factors served as a control alongside graded (+20% and 10% nHA/−TGF-β1), blended (+20% and 10% nHA/+bare TGF-β1), and spheres (+20% and 10% nHA/+TGF-β1 nanospheres) experimental groups. Cell seeded scaffolds were cultured in complete media without supplementation of morphogenetic factors for 1 and 2 weeks, respectively. Total DNA content per scaffold was quantified via Quant-iT™ PicoGreen® dsDNA Kit (Invitrogen, Carlsbad, Calif.). Briefly, a working solution of picogreen reagent in 1× Tris-EDTA buffer was prepared and added at a volume of 100 μL to 100 μL of DNA standard and sample solution in a 96-well plate, respectively. The well plate was read on a fluorescent spectrometer (Spectramax Gemini XPS, Molecular Devices, Sunnyvale, Calif.) with excitation at 485 nm and emission at 528 nm.

Glycosaminoglycan (GAG), a key component of cartilage matrix, was measured using a standard GAG assay kit (Accurate Chemical & Scientific Corp., Westbury, N.Y.) according to manufacturer's instructions. GAG content was quantified and presented as total GAG content per scaffold. Specifically, a predetermined volume of sample and buffer solution was added to a microcentrifuge tube with 500 μL of dye reagent and mixed for 30 minutes. The GAG-dye complex was centrifuged for 10 minutes at 10,000 g until a pellet was visible. The supernatant was decanted and all residual fluid was blotted dry. Next, 600 μL of dissociation reagent was added to the tubes and shaken for 30 minutes; 100 μL of each solution was placed into a 96-well plate and analyzed in triplicate. Absorbance was read at 656 nm and correlated to a standard curve of known standards.

Human type II collagen was evaluated via Type II collagen ELISA (Fisher Scientific, Pittsburgh, Pa.) per manufacturer's instruction. Briefly, lysed control and sample aliquots were added to pre-coated 96-well plates and incubated. Unbound sample was washed and collagen type II specific detection antibody was added incubated and washed. After washing, tetramethylbenzidine was added producing a color change. The reaction was stopped by the addition of an acidic stop solution and read at 450 nm.

Calcium deposition, one of the most important indicators of osteogenic differentiation, was measured using a calcium reagent kit (Pointe Scientific Inc.). Briefly, hMSCs were lysed through three freeze-thaw cycles and removed. The scaffolds containing deposited calcium and ECM were immersed in a 0.6 N HCl solution at 37° C. for 24 h. After the prescribed time period, the amount of dissolved calcium present in the acidic supernatant was measured by reacting with the o-cresolphthalein complexone to form a purple tinted solution. Absorbance was measured by a spectrophotometer at 570 nm. Total calcium deposition was calculated from standard curves of known calcium concentrations run in parallel with experimental groups and normalized to remove contributions associated with incorporated nHA.

Statistical Analysis

Data are presented as the mean value±standard error of the mean (StdEM) and were analyzed via one-way ANOVA and student's t-test to determine differences amongst the groups. Statistical significance was considered at $p<0.05$.

Results

Table-Top SL Printer Design, Cure Depth Analysis, and SL Printing of Porous Scaffolds The desire to produce complex 3D scaffolds for TE has driven researchers to explore a variety of fabrication technologies. 3D printing techniques, such as SL, are emerging as promising tools for scaffold fabrication. Here, we have developed a novel table-top SL printer to fabricate PEG-based bioactive nanocomposite scaffolds demonstrating the potential for creating multi-material, multi-layered structures. Several aspects of the current system mirror or outperform those of commercial SL systems (such as the Viper si2 SLA rapid prototyping system). The primary benefits include: quick and easy fabrication of multilayered material into a complex structure, lower cost ($10K vs. >$100K), similar spot size (190±50 μm vs. 250±25 μm (normal mode)), and comparable power output (~100 mW). Due to the ability to alter the frequency of the pulsed signal, power at the material's surface can be controlled with a range ~40-110 mW. But, unlike commercial systems, our printer is extremely modular owing to the use of a fiber-optically coupled UV laser source which can be readily fitted with off-the-shelf optics for fine or coarse printing. These results show the great promise of this system for successfully fabricating complex scaffolds using photocrosslinkable hydrogels.

Figure 15A:
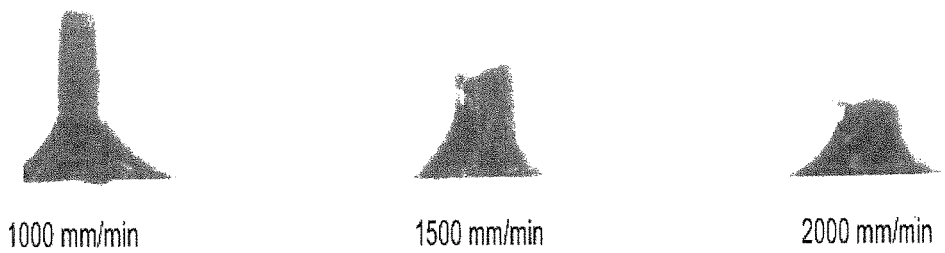
FIG. 15A shows an optical micrograph of cure depth samples.
Figure 15B:
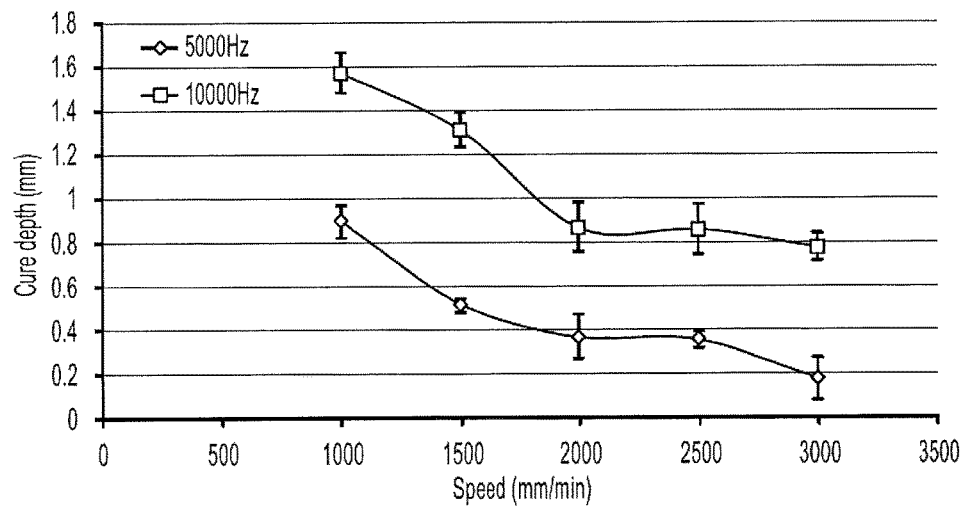
FIG. 15B is a cure depth plot.

In addition, we have performed initial cure depth studies in an effort to determine optimal printing parameters for adequate interlayer adhesion and resultant scaffold fabrication by examining the effect of print speed and laser frequency. It should be noted that the laser power per unit area for the data in this experiment is ~40 mW/cm2. Optical images of cure depth samples can be seen in FIG. 15 panel A with corresponding gel thickness (FIG. 15 panel B) curves as a function of print speed (mm/min) and laser frequency. FIG. 15A shows an Optical micrograph (panel A) of cure depth samples at 5000 Hz and cure depth plot (panel B) of pulsed laser UV crosslinking of 60% PEG-Da/PEG (wt %) at 5000 Hz and 10000 Hz.

Figure 16:
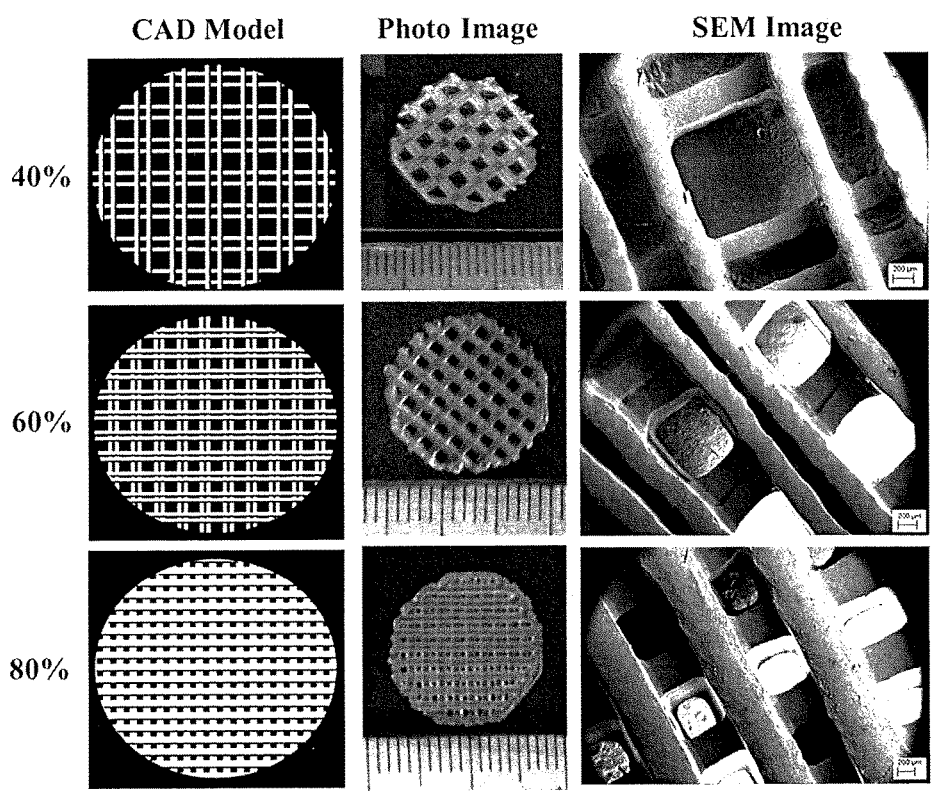
FIG. 16 shows CAD models, optical, and scanning electron micrographs of hydrogel scaffolds with varying in-fill densities.
Figure 17:
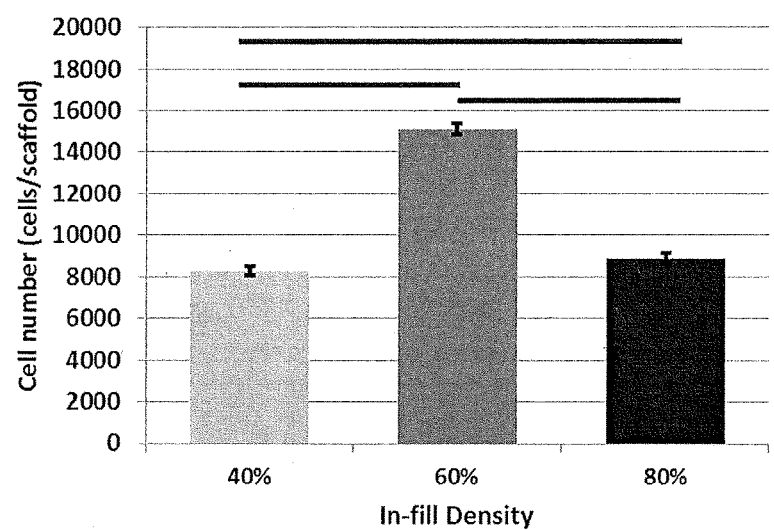
FIG. 17 shows a bar graph of hMSC adhesion on 3D printed hydrogel scaffolds of varying in-fill densities

For all subsequent studies, a print speed of 2000 mm/min and laser frequency of 5000 Hz was used in order to produce an effective and homogeneous layer thickness of 400 μm when adding 3 mL of nanobioink solution to a 10 cm diameter glass petri dish print substrate. FIG. 16 illustrates the CAD toolpath of the UV laser used in fabricating 15 mm diameter scaffolds of increasing solidity (40%, 60%, and 80%). FIG. 16 shows CAD models, optical, and scanning electron micrographs of hydrogel scaffolds with varying in-fill densities. Optical and SEM analysis (FIG. 16) show excellent corroboration between the pre-designed porous scaffold and resultant 3D printed structure with excellent horizontal and vertical microchannel formation. Scaffold properties and dimensions of each printed porous structure can be seen in Table 4. Based on the CAD model and SEM analysis, the effective spot size and line width were determined to be 215 μm with discernable high resolution lines for 40% and 60% in-fill density scaffolds. Interestingly, with increased in-fill density (80%) noticeable overlap of lines lead to an effective width of ~420 μm. Four-hour hMSC adhesion (FIG. 17) revealed a statistically significant increase upon 60% in-fill density samples which outperformed low and high in-fill density samples. FIG. 17 shows 4-hour hMSC adhesion on 3D printed hydrogel scaffolds of varying in-fill densities (Data are mean±StdEM, N=3, *$p<0.05$). This can be attributed to the presence of suitable pore size, surface area and porosity when compared to other in-fill densities. For all the following studies, an in-fill density of 60% was used.

TABLE 4

Dimensions and parameters of table-top SL 3D printed porous scaffolds

| In-fill Density | Surface Area | Volume | % Porosity | SA/V Ratio | Line Width | Max Pore Size |
|---|---|---|---|---|---|---|
| 40% | 408.9 mm$^2$ | 28.1 mm$^3$ | 79.6 | 14.6 | 215 μm | 1250 μm |
| 60% | 613.8 mm$^2$ | 42.3 mm$^3$ | 69.3 | 14.5 | 215 μm | 790 μm |
| 80% | 718.3 mm$^2$ | 71.4 mm$^3$ | 48.2 | 10.1 | 420 μm | 500 μm |

Figure 18:
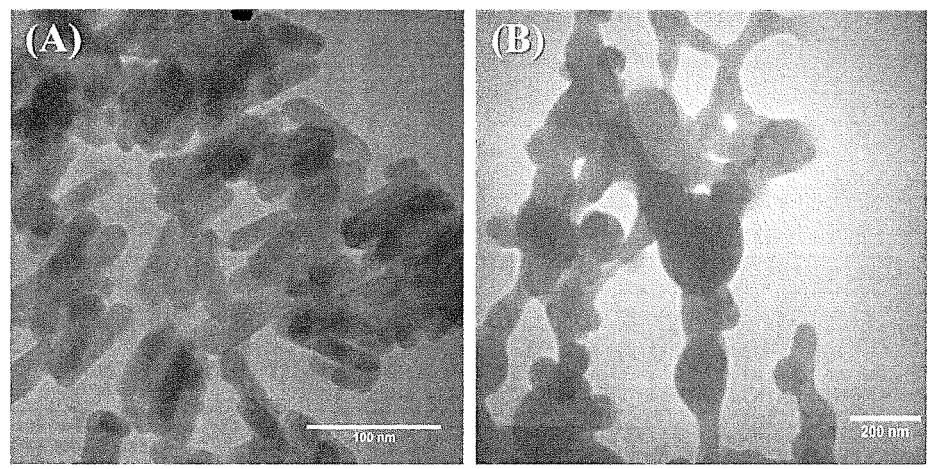
FIG. 18 shows Transmission Electron Microscopy (TEM) images of hydrothermally treated nHA and TGF-β1 encapsulated nanospheres.
Figure 19:
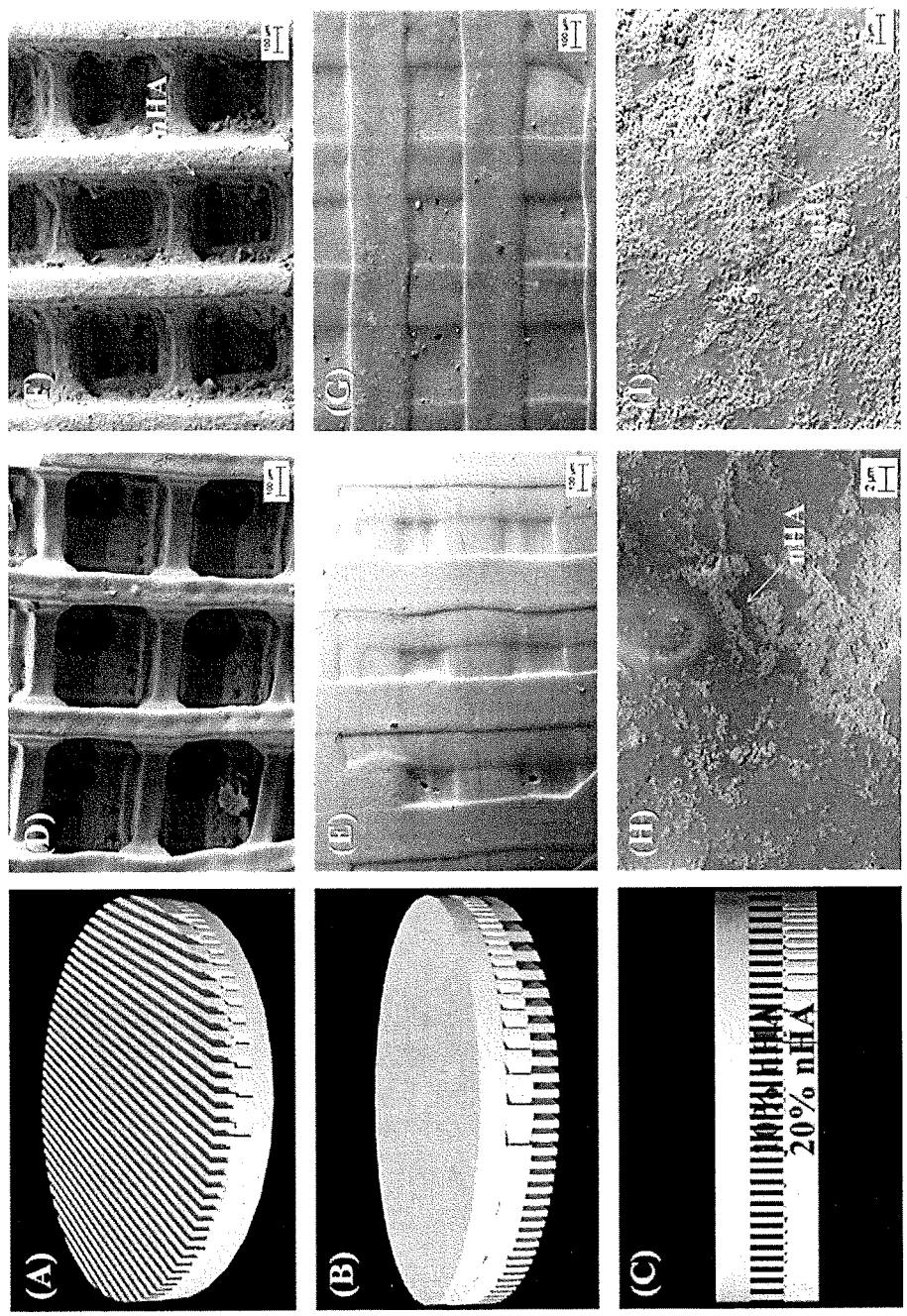
FIG. 19 shows 3D CAD model of the three-layer osteochondral scaffold design, SEM images of control scaffolds and osteochondral scaffolds with graded nHA.
Figure 20:
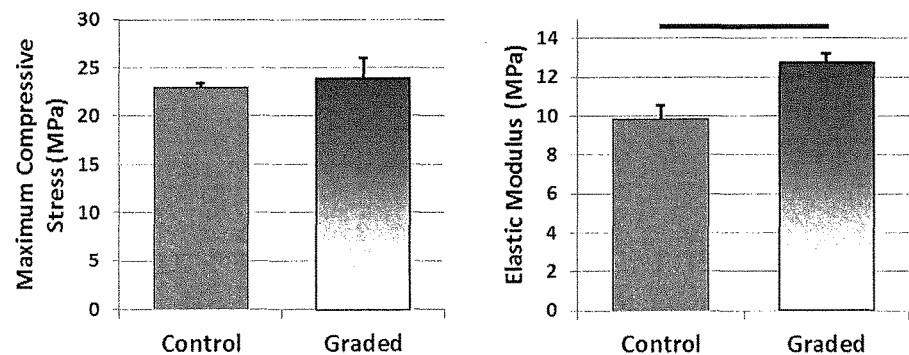
FIG. 20 shows bar graphs showing results for uniaxial compression testing of three-layer 3D printed control and graded nHA scaffolds.

Nanobioink characterization and bioactive graded osteochondral scaffold fabrication Morphological analysis of synthesized nHA displayed grain sizes in the range of 80-100 nm (FIG. 18 panel A) in length and PLGA nanospheres (FIG. 18 panel B) on the order of 75±17 nm in diameter. FIG. 18 shows TEM images of hydrothermally treated nHA (panel A) and TGF-β1 encapsulated nanospheres (panel B). Based on the ease by which the composition of each layer can be altered, the table-top SL printer was used to 3D print a three-layer graded osteochondral scaffold exhibiting a solid articular cartilage layer and 10% and 20% nHA middle and bottom layer to serve as the calcified transitional zone and subchondral region. FIG. 19 panels A-C show the CAD model design of the 3D graded osteochondral scaffold. Retention of printability is evident upon SEM evaluation (FIG. 19) of scaffold morphology. FIG. 19 shows (in panels A-C) 3D CAD model (bottom, top and side view) of the three-layer osteochondral scaffold design with 60% in-fill density. SEM images of control scaffolds without nHA (bottom and top images) are shown in FIG. 19 panels D-E; and FIG. 19 panels F-I show osteochondral scaffolds with graded nHA (panel F is the bottom, panel G is the top; panel H is 10% nHA layer and I is 20% nHA layer). In addition, SEM image analysis (FIG. 19 panels H-I) reveals a more biomimetic scaffold with respect to nanotexturization and bioactivity in the presence of 10% and 20% nHA when compared to the controls, as well as aids in enhancing the compressive strength of the overall scaffold (FIG. 20). FIG. 20 shows uniaxial compression testing of three-layer 3D printed control and graded nHA scaffolds. FIG. 20, panel A shows graded scaffolds display a similar max load and a 29% increase in elastic modulus (shown in FIG. 20 panel B) when compared to control. (Data are mean+StdEM, n=5, *$p<0.05$).

A 29% increase in compressive modulus was observed in the graded osteochondral scaffold when compared to non-nHA control.

Figure 21:
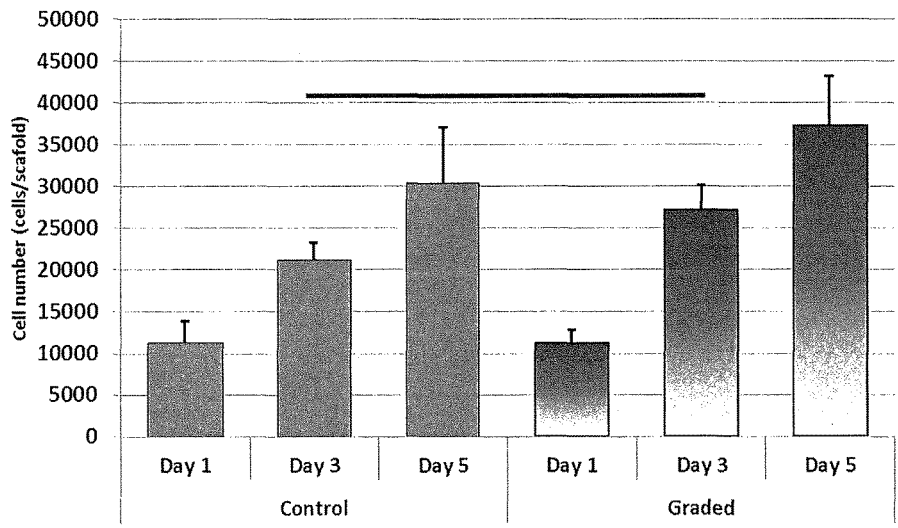
FIG. 21 shows a bar graph of five-day hMSC proliferation on 3D printed osteochondral scaffolds.
Figure 22:
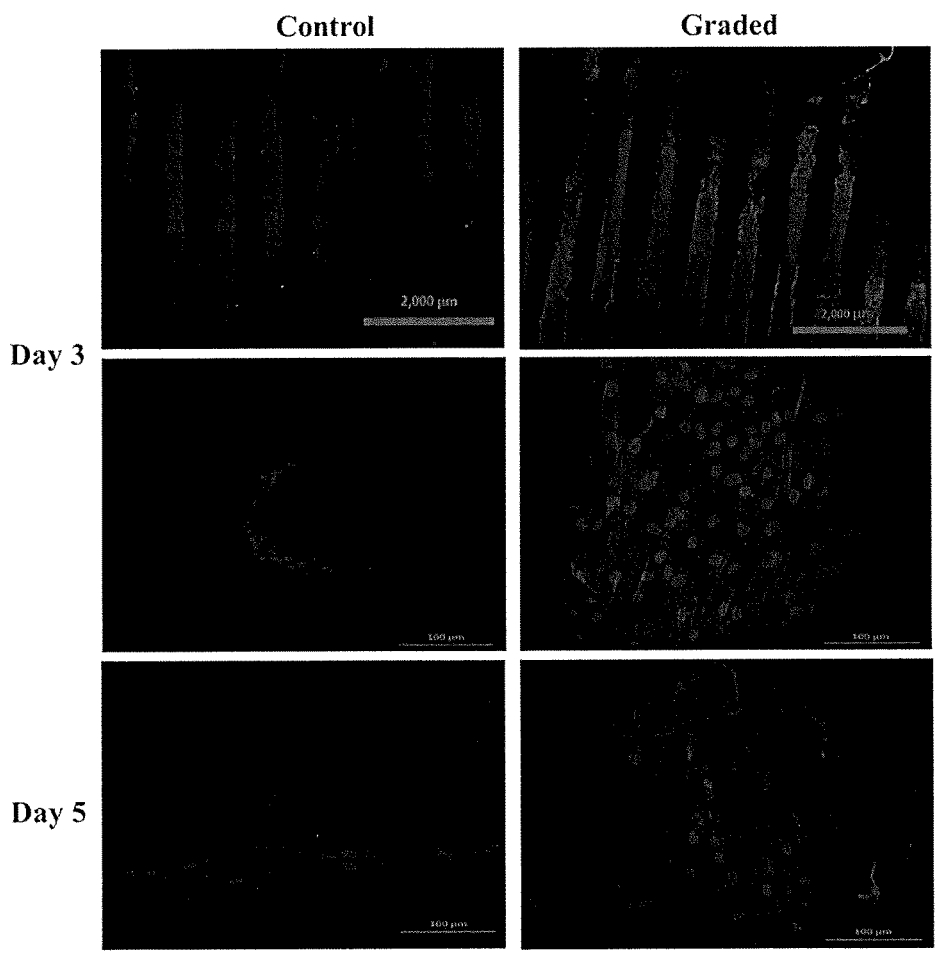
FIG. 22 shows three and five-day hMSC spreading morphology on 3D printed scaffolds.

In addition to enhanced compressive strength, a five-day hMSC proliferation study was performed (FIG. 21). FIG. 21 shows five-day hMSC proliferation on 3D printed osteochondral scaffolds containing spatially distributed nHA. (Data are mean±StdEM, N=3, *$p<0.05$). With the incorporation of nHA nanoparticles, a more than 20% increase in cell density was observed after 3 day culture. In addition, as shown in FIG. 22, three and five-day hMSC spreading morphology on 3D printed scaffolds containing spatially distributed nHA was greatly enhanced when compared to controls. FIG. 22 shows three and five-day hMSC spreading morphology on 3D printed scaffolds containing spatially distributed nHA when compared to controls. After three days of culture, hMSCs display excellent spreading when compared to the spherical morphology of hMSCs seeded upon control scaffolds. In addition, increased cell growth density can be seen as illustrated through DAPI staining of cell nuclei. After three days of culture, hMSCs display excellent spreading when compared to the spherical morphology of hMSCs seeded upon control scaffolds which can be correlated to an increase in nanotexturization and resultant increase in surface area.

Figure 23:
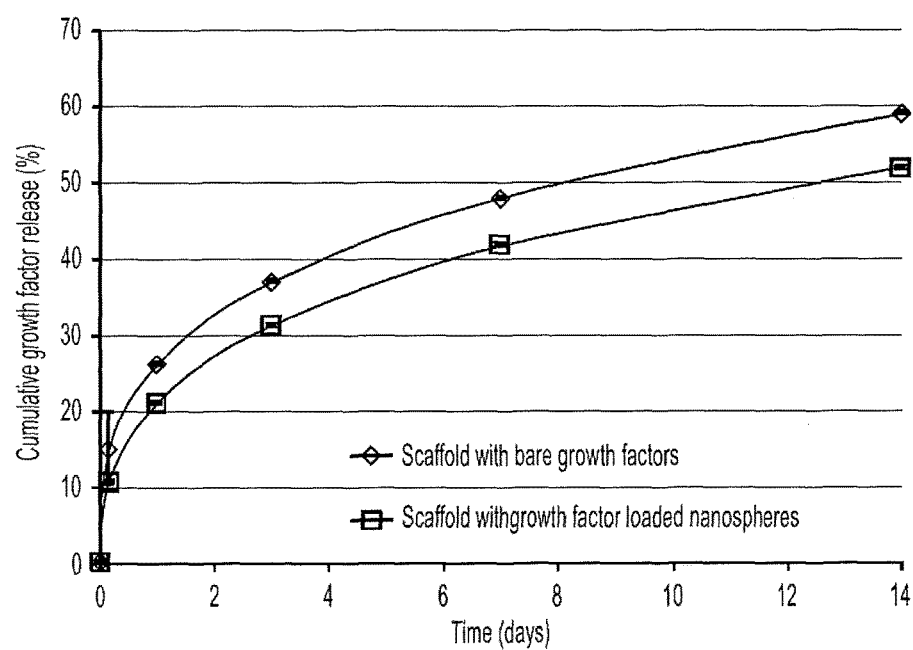
FIG. 23 shows a graph of results from a two-week TGF-β1 release study of blended and nanosphere encapsulated growth factors within the articulating cartilage layer of graded nHA scaffolds.

Furthermore, a growth factor release study was conducted to determine TGF-β1 release kinetics of the nanocomposite osteochondral scaffold developed here. FIG. 23 shows the cumulative release profiles of bare TGF-β1 and TGF-β1 encapsulated nanospheres within a graded scaffold. Both scaffolds can sustainably release growth factors over 14 days. FIG. 23 shows a two-week TGF-β1 release study of blended and nanosphere encapsulated growth factors within the articulating cartilage layer of graded nHA scaffolds. (Data are mean±StdEM, n=3). In particular, the PLGA nanosphere-containing scaffolds exhibited further inhibited initial burst release and steady TGF-β1 delivery over 14 days when compared non-nanosphere samples. In addition, due to the extreme flexibility of the co-axial system, a wide range of polymers can be readily used as encapsulants for sustained delivery.

Figure 24:
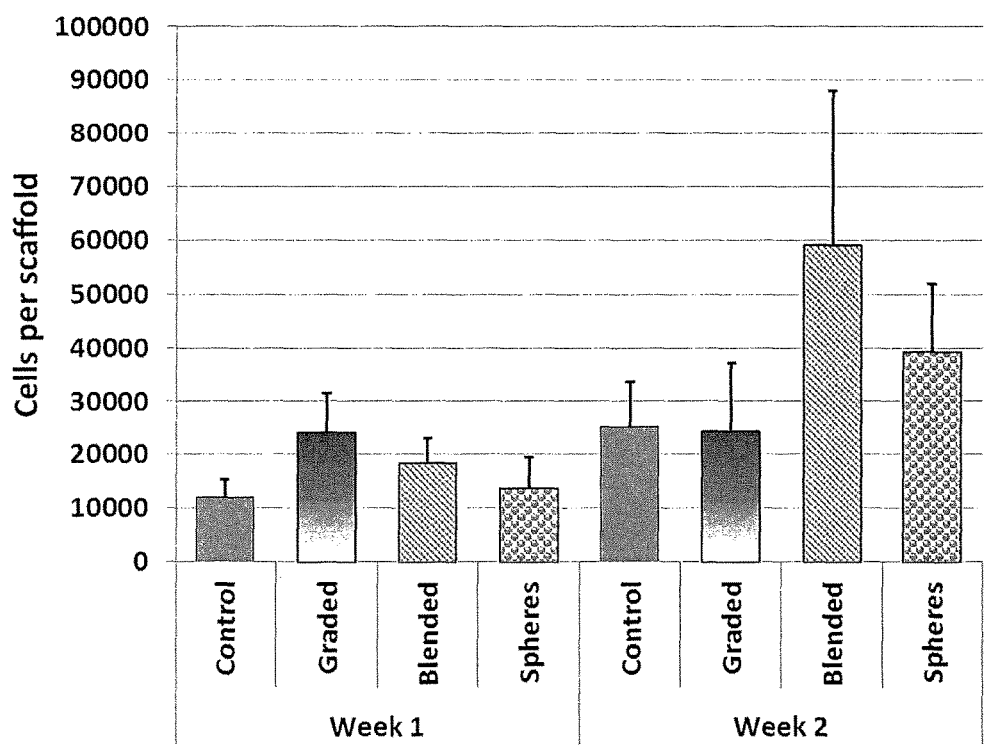
FIG. 24 shows bar graphs from the two-week total DNA content of hMSC seeded control, graded, and TGF-β1 incorporated osteochondral scaffolds.

Enhanced hMSC chondrogenic and osteogenic differentiation upon bioactive graded osteochondral scaffolds containing osteogenic nHA and chondrogenic TGF-β1 nanospheres For hMSC osteochondral differentiation studies, the bioactive osteochondral scaffold was evaluated for chondrogenic and osteogenic differentiation potential, respectively. Seeded samples were evaluated for total DNA content, GAG, type II collagen, and extracellular calcium deposition after two weeks of culture. FIG. 24 shows total DNA content corresponding to cell number per scaffold. There is no significant difference of hMSC density amongst the sample groups. FIG. 24 shows the two-week total DNA content of hMSC seeded control, graded, and TGF-β1 incorporated osteochondral scaffolds. TGF-β1 containing scaffolds showed a slight increase in cell number for blended and nanosphere groups from week 1 to week 2, respectively. (Data are mean±StdEM, N=3).

Figure 25:
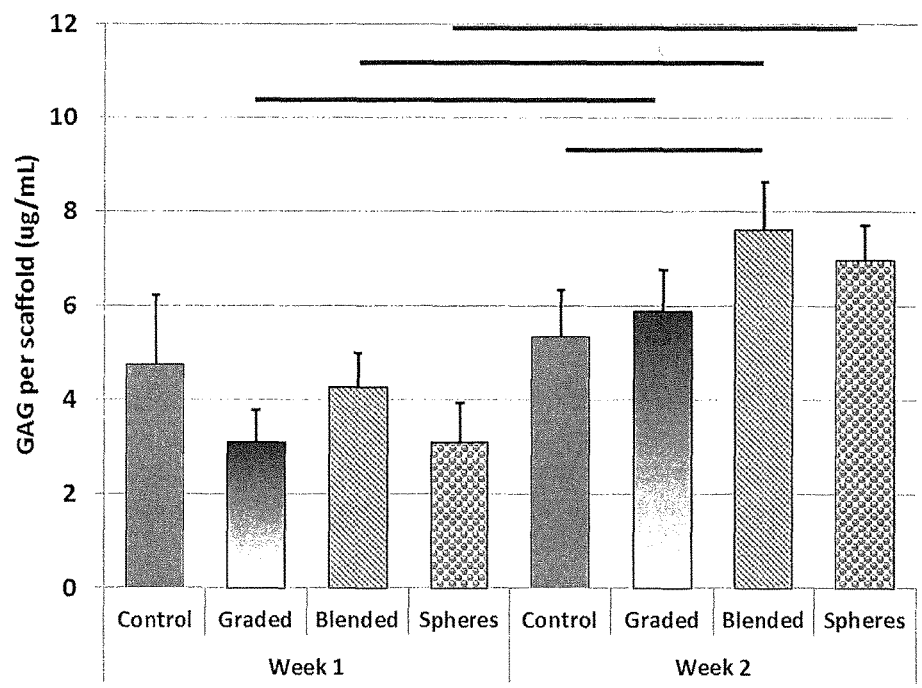
FIG. 25 shows bar graphs showing the two-week hMSC GAG production.
Figure 26:
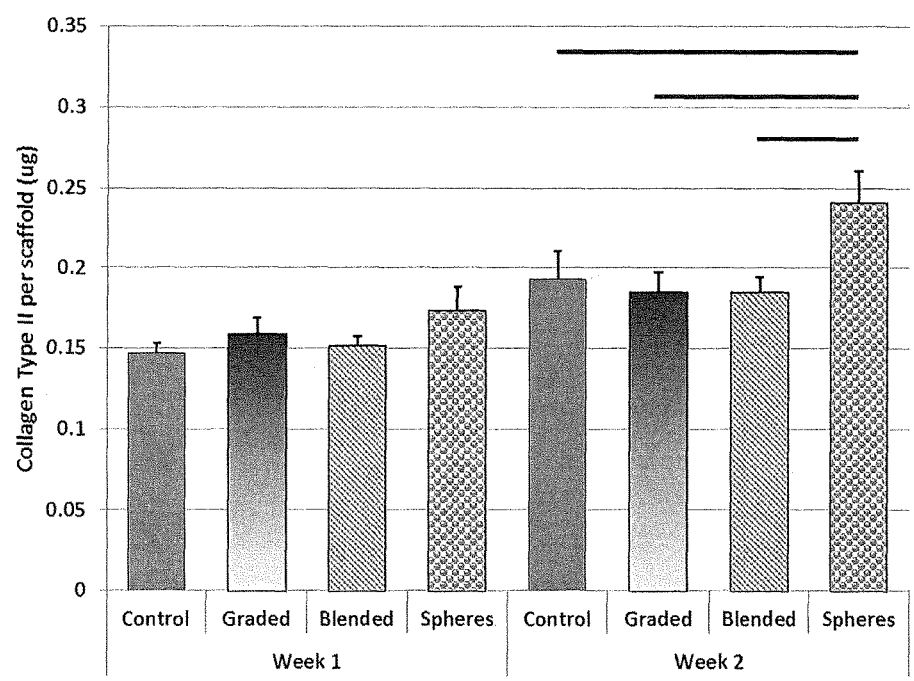
FIG. 26 shows bar graphs showing the two-week hMSC collagen type II production.

FIG. 25 shows a significant increase in GAG production upon TGF-β1 incorporated scaffolds (blended) at week 2 when compared to controls. FIG. 25 shows two-week hMSC GAG production. All nHA containing scaffolds at week 2 showed a significant increase in GAG production when compared to week 1. (Data are mean±StdEM, N=3, *p<0.05). All nHA-containing scaffolds exhibited a significant increase in GAG production after two weeks when compared to week 1. Graded scaffolds yielded a 90% increase with bare TGF-β1 inducing a 78% increase and PLGA nanosphere containing samples outperforming all other sample groups with an increase of 126% from week 1 to week 2. In addition, FIG. 26 illustrates another important cartilage matrix protein—type II collagen synthesis in bioactive graded osteochondral scaffolds. FIG. 26 shows two-week hMSC collagen type II production. TGF-β1 encapsulated nanospheres incorporated within graded nHA scaffolds showed the greatest collagen production after two weeks when compared to all other groups. (Data are mean±StdEM, N=3, *p<0.05).

As a late-stage marker of chondrogenic differentiation, type II collagen synthesis showed 25%-30% increases after two weeks for TGF-β1 encapsulated nanosphere scaffolds when compared to control and all other experimental groups.

Figure 27:
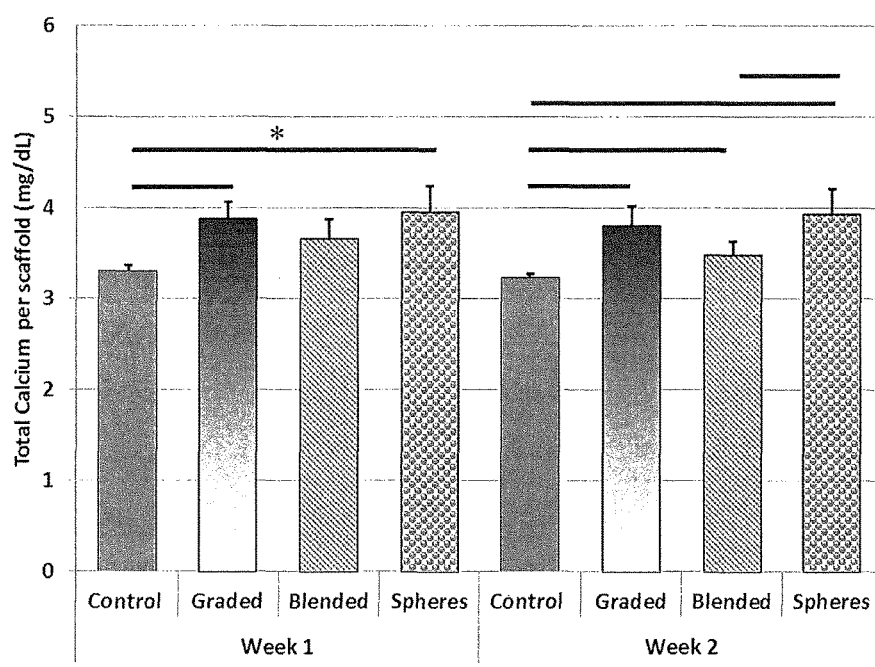
FIG. 27 shows bar graphs showing the two-week hMSC total calcium deposition.

In addition to improved chondrogenic differentiation, our osteochondral scaffold with nHA and TGF-β1 are promising for enhanced osteogenic differentiation of hMSCs. In particular, deposited extracellular calcium results (FIG. 27) revealed greater calcium deposition amongst graded and TGF-β1 encapsulated nanosphere-containing samples after one week of culture when compared to control. FIG. 27 shows two-week hMSC total calcium deposition. nHA containing scaffolds showed a significant increase in total extracellular calcium deposition after one and two weeks of culture when compared to control. TGF-β1 encapsulated nanospheres incorporated within graded nHA scaffolds showed the greatest extracellular calcium deposition after two weeks. (Data are mean±StdEM, N=3, *p<0.05). After two weeks, all sample groups displayed enhanced extracellular calcium deposition when compared to control. Both, graded and nanosphere containing nanocomposite scaffolds, exhibited increased extracellular calcium deposition of 17% and 18% after one week and a 20% and 22% increase after 2 weeks culture, respectively, when compared to control. Taken collectively, all of the above data reveal the great potential of this novel 3D printing system and graded bioactive nanocomposite scaffold for efficient delivery of TGF-β1, creating nano surface topography and subsequent improved growth, chondrogenic/osteogenic differentiation of hMSCs.

Discussion

Table-Top SL Printing for the Fabrication of Bioactive Graded Nanocomposite Scaffolds with Sustained Bioactive Factor Delivery The novel 3D printing system developed here allows for the rapid fabrication of photocrosslinkable hydrogel scaffolds with efficient and effective incorporation of nanobiomaterials leading to increased nanoscale surface roughness and highly porous geometry. In addition, modifications to the 3D model can be readily made where each respective layer's in-fill density (corresponding to pore density) and orientation can be readily controlled creating a gradual transition of bioactivity and geometry. The composition of the 3D printed scaffold can be customized to regenerate a particular tissue type through the incorporation of tissue-specific organic and inorganic components in a highly reproducible manner.

Surface topography is an important feature when designing scaffolds for tissue engineering applications.[84] The 3D osteochondral scaffold developed here integrated bioactive inorganic nano ceramics and nanosphere growth factor delivery for a cell-favorable surface topography. Specifically, one of the key nanomaterials utilized in the manufacture of our graded osteochondral scaffold, nHA, can provide several key benefits to include: mechanical reinforcement, nanotexturization, and osteoconductivity. As a bioactive and osteoconductive chemical component in bone and the calcified zone in cartilage,[39-41] hydroxyapatite and its chemical derivatives have been extensively studied and shown to increase cell-scaffold performance via incorporation within a bulk matrix[53] as well as surface adsorption[87-89] and in situ nucleation.[90-92] Through a hydrothermal treatment method, our lab readily synthesizes biomimetic nHA with excellent control of nano scale crystallinity and surface morphology. Our hydrothermally treated nHA serves as an excellent mechanical reinforcer within our 3D printed osteochondral construct. Furthermore, the capacity of 3D printed scaffolds to withstand compressive loads is important due to the fact that human osteochondral tissue in joints is under repetitive compressive loading on a daily basis. Tissue degeneration emanating from injuries to the cartilage layer is largely exacerbated by mismatches in implant-host tissue stiffness. The scaffolds fabricated here display compressive strength similar to that of native osteochondral tissue and other reported biphasic systems therefore rendering the fabricated scaffold less likely to fail.[3]

In addition, the incorporation of PLGA nanospheres was employed as a sustained delivery device which promoted synergistic interactions when combined with other incorporated nanobiomaterials as evidenced by controlled and sustained bioactive factor delivery. It is well known that various growth factors (e.g., TGF-β1) have been shown to improve hMSC osteogenic and chondrogenic differentiation[41-43]. Unfortunately, for in vivo applications, these growth factors face ongoing issues related to short-term retention, quick half-life in circulation, and quick loss of biological activity even when administered at high doses. Therefore, we extended the application of the scaffold design to not only serve as a 3D structural support for cellular attachment, but as a sustained TGF-β1 delivery device for long-term osteochondral tissue regeneration. A significant decrease in growth factor release was observed and is postulated to be attributed to differences in biomaterial degradation where low molecular weight PEGs degrade at a quicker rate than PLGA-based polymers.[93,94] Therefore, by utilizing PLGA as the nanosphere material, inhibited degradation can be achieved. In addition, electrostatic interactions amongst the negative carboxyl terminals of the globular protein and positively-charged species ($H^+$ and $Ca^{2+}$) of the nHA particles present at the material's surface[37] as well as electrostatic interactions of the bulk hydrogel matrix may also contribute retention of growth factor.

Enhanced hMSC function and osteochondral matrix development within 3D printed bioactive graded scaffolds Scaffolds with a highly interconnected microporous calcified transitional and subchondral region were created which facilitated cell adhesion, proliferation, and cellular activities. Similar to observations reported by Knychala et al.[95] 3D scaffolds with smaller pores elicit greater cellular differentiation which is corroborated with our finding of fabricated scaffolds small pores outperforming scaffolds with larger pores. This porous structure allows for efficient exchange of nutrients and metabolic waste removal during new tissue formation. Through the incorporation of osteoconductive nHA, hMSC growth was enhanced. Our cell studies confirmed that the synthesized nHA can be an excellent osteoconductive chemical cue for improving hMSC proliferation and early osteogenesis in vitro. Qualitative evaluation of hMSC growth morphology reveal increased cell density and excellent cell spreading as noted by the extension of filopodia.

The notable increase in GAG production upon TGF-β1 containing samples is postulated to be directly related to sustained growth factor release and synergetic interactions of growth factor and nHA particles. Bare TGF-β1 samples lead to increased GAG production after two weeks of culture as illustrated by decreased release kinetics. Tezcan et al.[49] revealed a dose-dependent response of TGF-β1 induced hMSC chondrogenic differentiation wherein TGF-β1 was critical in the initiation of GAG synthesis and late stage tissue maturation. Although TGF-β1 was added only to the top cartilage layer, localized diffusion through the entire construct is facilitated by the inherent microporous nature of the PEG-Da hydrogel whose composition consisted of a 40% soluble fraction as characterized in our previous work.[53] In addition, type II collagen and extracellular calcium deposition increased upon PLGA nanosphere scaffolds providing further evidence of bioactive nanosphere upon improving osteochondral tissue formation. Schagemann et al.[96] described the effects of hydroxyapatite on initial cell adhesion combined with the introduction of TGF-β1 for the induction of osteogenic gene expression. It was found that sustained growth factor presence inhibited Type I collagen, but increased Type II collagen expression similar to the results presented here. No statistical difference was noted between blended and spheres samples with request to cell density and GAG production, but was statistically lower for latter stage differentiation markers showing that lower doses and sustained growth factor release through the incorporation of nanospheres enhanced MSC differentiation. In addition, more favorable surface topography and steric interactions of biological constituents in the presence of PLGA nanospheres when compared to hydrogel alone in concert with extended release may lead to expedited tissue formation as evident by the increase in late-stage ECM markers.

Conclusions:

The work presented herein served to illustrate the efficacy of the nano-ink and current table-top SL 3D printing technology for efficient fabrication of a novel graded nanocomposite osteochondral scaffold with predesigned micro architecture and controlled factor release. hMSC proliferation, and osteochondral differentiation were greatly enhanced through the incorporation of tissue-specific nHA and TGF-β1 encapsulated nanospheres. Moreover, due to the flexible design nature of our printing system and CAD modeling, a variety of complex tissue or even organ scaffolds with nanomaterials and growth factors can be readily fabricated, thus make them promising for diverse tissue and organ regeneration applications.

REFERENCES

1. Zhang L, Webster T J. Nanotechnology and nanomaterials: Promises for improved tissue regeneration. Nano Today. 2009; 4(1):66-80.
2. Zhang L, Sirivisoot S, Balasundaram G, Webster T J. Nanoengineering for Bone Tissue Engineering. In: Khademhosseini A, Borenstein J, Toner M, Takayama S, eds. Micro and Nanoengineering of the Cell Microenvironment: Technologies and Applications: Artech House; 2008:431-460.
3. Zhang L, Hu J, Kyriacos A. Athanasiou. The Role of Tissue Engineering in Articular Cartilage Repair and Regeneration. Critical reviews in biomedical engineering. 2009; 37(1-2):1-57.
4. Wang M, Castro N J, Li J, Keidar M, Zhang L G. Enhanced Osteoblast and Mesenchymal Stem Cell Functions on Titanium with Biomimetic Hydrothermally Treated Nanocrystalline Hydroxyapatite/Magnetically Synthesized Carbon Nanotubes for Orthopedic Applications. of Biomedical Materials Research Part B. 2012: Submitted.
5. Im O, Li J, Wang M, Zhang L G, Keidar M. Biomimetic three-dimensional nanocrystalline hydroxyapatite and magnetically synthesized single-walled carbon nanotube chitosan nanocomposite for bone regeneration. Int J Nanomedicine. 2012; 7:2087-2099.

6. Castro N, Hacking S, Zhang L. Recent Progress in Interfacial Tissue Engineering Approaches for Osteochondral Defects. Ann Biomed Eng. 2012; 40(8):1628-1640.
7. Temenoff J S, Yang P J. Engineering Orthopedic Tissue Interfaces. Tissue Eng Part B-Re. June 2009; 15(2):127-141.
8. Zhang L, Li J Y, Lee J D. Nanotechnology for Cartilage and Bone Regeneration. In: Webster T J, ed. Nanomedicine: technologies and applications: Woodhead Publishing Limited; 2012:571-598.
9. Fu S W, Chen L, Man Y-G. miRNA Biomarkers in Breast Cancer Detection and Management. J Cancer. 2011; 1(2): 116-122.
10. Langer R, Vacanti J P. Tissue Engineering. Science. May 14, 1993; 260(5110):920-926.
11. Zhang L, Rodriguez J, Raez J, Myles A J, Fenniri H, Webster T J. Biologically inspired rosette nanotubes and nanocrystalline hydroxyapatite hydrogel nanocomposites as improved bone substitutes. Nanotechnology. Apr. 29, 2009; 20(17):175101.
12. Zhang L, Sirivisoot, S., Balasundaram, G., and Webster, T. J. Nanomaterials for Improved Orthopedic and Bone Tissue Engineering Applications. In: Basu B. D K, A. Kuma, ed. Advanced Biomaterials: Fundamentals, Processing and Application: John Wiley & Sons Inc.; 2009: 205-241.
13. Arcaute K, Mann B K, Wicker R B. Stereolithography of three-dimensional bioactive poly(ethylene glycol) constructs with encapsulated cells. Ann Biomed Eng. September 2006; 34(9):1429-1441.
14. Colter D C, Class R, DiGirolamo C M, Prockop D J. Rapid expansion of recycling stem cells in cultures of plastic-adherent cells from human bone marrow. Proc Natl Acad Sci USA. Mar. 28, 2000; 97(7):3213-3218.
15. de Boer R, Knight A M, Spinner R J, Malessy M J, Yaszemski M J, Windebank A J. In vitro and in vivo release of nerve growth factor from biodegradable poly-lactic-co-glycolic-acid microspheres. J Biomed Mater Res A. Dec. 15, 2010; 95(4):1067-1073.
16. Dawes G J, Fratila-Apachitei L E, Necula B S, Apachitei I, Witkamp G J, Duszczyk J. Release of PLGA-encapsulated dexamethasone from microsphere loaded porous surfaces. Journal of materials science. Materials in medicine. January 2010; 21(1):215-221.
17. Dawes G J, Fratila-Apachitei L E, Mulia K, Apachitei I, Witkamp G J, Duszczyk J. Size effect of PLGA spheres on drug loading efficiency and release profiles. Journal of materials science. Materials in medicine. May 2009; 20(5):1089-1094.
18. Bouffi C, Thomas O, Bony C, et al. The role of pharmacologically active microcarriers releasing TGF-beta3 in cartilage formation in vivo by mesenchymal stem cells. Biomaterials. September 2010; 31(25):6485-6493.
19. Elisseeff J, McIntosh W, Fu K, Blunk B T, Langer R. Controlled-release of IGF-I and TGF-beta1 in a photopolymerizing hydrogel for cartilage tissue engineering. J Orthop Res. November 2001; 19(6):1098-1104.
20. Graves R A, Poole D, Moiseyev R, Bostanian L A, Mandal T K. Encapsulation of indomethacin using coaxial ultrasonic atomization followed by solvent evaporation. Drug Dev Ind Pharm. April 2008; 34(4):419-426.
21. Solorio L D, Fu A S, Hernandez-Irizarry R, Alsberg E. Chondrogenic differentiation of human mesenchymal stem cell aggregates via controlled release of TGF-beta1 from incorporated polymer microspheres. J Biomed Mater Res A. Mar. 1, 2010; 92(3):1139-1144.
22. Verreck G, Chun I, Li Y, et al. Preparation and physicochemical characterization of biodegradable nerve guides containing the nerve growth agent sabeluzole. Biomaterials. 2005; 26(11):1307-1315.
23. Liu J, Jiang Z, Zhang S, et al. Biodegradation, biocompatibility, and drug delivery in poly(o-pentadecalactone-co-p-dioxanone) copolyesters. Biomaterials. 2011; 32(27):6646-6654.
24. Zhang L, Feng Y, Tian H, Shi C, Zhao M, Guo J. Controlled release of doxorubicin from amphiphilic depsipeptide-PDO-PEG-based copolymer nanosized microspheres. Reactive and Functional Polymers. 2013; 73(9): 1281-1289.
25. Almeria B, Deng W, Fahmy T M, Gomez A. Controlling the morphology of electrospray-generated PLGA microparticles for drug delivery. J Colloid Interface Sci. Mar. 1 2010; 343(1):125-133.
26. Panusa A, Selmin F, Rossoni G, Carini M, Cilurzo F, Aldini G. Methylprednisolone-loaded PLGA microspheres: a new formulation for sustained release via intra-articular administration. A comparison study with methylprednisolone acetate in rats. J Pharm Sci. November 2011; 100(11):4580-4586.
27. Stevanovic M, Uskokovic D. Poly(lactide-co-glycolide)-based Micro and Nanoparticles for the Controlled Drug Delivery of Vitamins. Curr Nanosci. February 2009; 5(1): 1-14.
28. Thomas V, Zhang X, Vohra Y K. A biomimetic tubular scaffold with spatially designed nanofibers of protein/PDS bio-blends. Biotechnol Bioeng. Dec. 1, 2009; 104 (5):1025-1033.
29. Venclauskas L, Grubinskas I, Mocevicius P, Kiudelis M. Reinforced tension line versus simple suture: a biomechanical study on cadavers. Acta chirurgica Belgica. September-October 2011; 111(5):288-292.
30. Sakamoto A, Kiyokawa K, Rikimaru H, Watanabe K, Nishi Y. An investigation of the fixation materials for cartilage frames in microtia. Journal of plastic, reconstructive & aesthetic surgery: JPRAS. May 2012; 65(5): 584-589.
31. Zhu J, Dang H C, Wang W T, Wang X L, Wang Y Z. Cellulose diacetate-g-poly(p-dioxanone) co-polymer: synthesis, properties and microsphere preparation. Journal of biomaterials science. Polymer edition. 2011; 22(8): 981-999.
32. Wang X L, Chen Y Y, Wang Y Z. Synthesis of poly(p-dioxanone) catalyzed by Zn L-lactate under microwave irradiation and its application in ibuprofen delivery. Journal of biomaterials science. Polymer edition. 2010; 21(6): 927-936.
33. Madurantakam P A, Rodriguez I A, Cost C P, et al. Multiple factor interactions in biomimetic mineralization of electrospun scaffolds. Biomaterials. October 2009; 30(29):5456-5464.
34. Smith M J, McClure M J, Sell S A, et al. Suture-reinforced electrospun polydioxanone-elastin small-diameter tubes for use in vascular tissue engineering: a feasibility study. Acta Biomater. January 2008; 4(1):58-66.
35. Kalfa D, Bel A, Chen-Tournoux A, et al. A polydioxanone electrospun valved patch to replace the right ventricular outflow tract in a growing lamb model. Biomaterials. May 2010; 31(14):4056-4063.
36. Kwon S H, Lee T J, Park J, et al. Modulation of BMP-2-induced chondrogenic versus osteogenic differ- 37. Tarafder S, Banerjee S, Bandyopadhyay A, Bose S. Electrically polarized biphasic calcium phosphates: adsorption and release of bovine serum albumin. Langmuir. November 16 2010; 26(22):16625-16629.
38. Noel D, Gazit D, Bouquet C, et al. Short-term BMP-2 expression is sufficient for in vivo osteochondral differentiation of mesenchymal stem cells. Stem Cells. 2004; 22(1):74-85.
39. Sekiya I, Colter D C, Prockop D J. BMP-6 enhances chondrogenesis in a subpopulation of human marrow stromal cells. Biochem Biophys Res Commun. Jun. 8, 2001; 284(2):411-418.
40. Bai X, Li G, Zhao C, Duan H, Qu F. BMP7 induces the differentiation of bone marrow-derived mesenchymal cells into chondrocytes. Med Biol Eng Comput. June 2011; 49(6):687-692.
41. Chim H, Miller E, Gliniak C, Alsberg E. Stromal-cell-derived factor (SDF) 1-alpha in combination with BMP-2 and TGF-beta1 induces site-directed cell homing and osteogenic and chondrogenic differentiation for tissue engineering without the requirement for cell seeding. Cell Tissue Res. October 2012; 350(1):89-94.
42. Kim M, Erickson I E, Choudhury M, Pleshko N, Mauck R L. Transient exposure to TGF-beta3 improves the functional chondrogenesis of MSC-laden hyaluronic acid hydrogels. Journal of the mechanical behavior of biomedical materials. July 2012; 11:92-101.
43. Ertan A B, Yilgor P, Bayyurt B, et al. Effect of double growth factor release on cartilage tissue engineering. Journal of tissue engineering and regenerative medicine. Nov. 14, 2011.
44. Kwon S H, Lee T J, Park J, et al. Modulation of BMP-2-induced chondrogenic versus osteogenic differentiation of human mesenchymal stem cells by cell-specific extracellular matrices. Tissue engineering. Part A. January 2013; 19(1-2):49-58.
45. Davis H E, Case E M, Miller S L, Genetos D C, Leach J K. Osteogenic Response to BMP-2 of hMSCs Grown on Apatite-Coated Scaffolds. Biotechnol Bioeng. November 2011; 108(11):2727-2735.
46. Huang W B, Carlsen B, Wulur I, et al. BMP-2 exerts differential effects on differentiation of rabbit bone marrow stromal cells grown in two-dimensional and three-dimensional systems and is required for in vitro bone formation in a PLGA scaffold. Exp Cell Res. October 1 2004; 299(2):325-334.
47. Kim J, Kim I S, Cho T H, et al. Bone regeneration using hyaluronic acid-based hydrogel with bone morphogenic protein-2 and human mesenchymal stem cells. Biomaterials. April 2007; 28(10):1830-1837.
48. Kim S E, Rha H K, Surendran S, et al. Bone morphogenic protein-2 (BMP-2) immobilized biodegradable scaffolds for bone tissue engineering. Macromol Res. October 2006; 14(5):565-572.
49. Tezcan B, Serter S, Kiter E, Tufan A C. Dose dependent effect of C-type natriuretic peptide signaling in glycosaminoglycan synthesis during TGF-beta1 induced chondrogenic differentiation of mesenchymal stem cells. Journal of molecular histology. October 2010; 41(4-5): 247-258.
50. Collins, G., J. Federici, et al. Charge generation, charge transport, and residual charge in the electrospinning of polymers: A review of issues and complications. Journal of Applied Physics 111(4). 2012.
51. G. W. Tang, H. Zhang, Y. H. Zhao, Y. Zhang, X. L. Li and X. Y. Yuan, *J Biomat Sci-Polym E*, 2012, 23, 2241-2257
52. P. Sibilla, A. Sereni, G. Aguiari, M. Banzi, E. Manzati, C. Mischiati, L. Trombelli and L. del Senno, *J Dent Res*, 2006, 85, 354-358
53. N. J. Castro, C. M. O'Brien and L. G. Zhang, *Aiche J*, 2014, 60, 432-442.
54. X. Z. Zhou, V. Y. Leung, Q. R. Dong, K. M. Cheung, D. Chan and W. W. Lu, *Int J Artif Organs*, 2008, 31, 480-489.
55. J. I. Dawson, D. A. Wahl, S. A. Lanham, J. M. Kanczler, J. T. Czernuszka and R. O. Oreffo, *Biomaterials*, 2008, 29, 3105-3116
56. I. O. Smith, X. H. Liu, L. A. Smith and P. X. Ma, *Wiley Interdisciplinary Reviews-Nanomedicine and Nanobiotechnology*, 2009, 1, 226-236.
57. T. Weigel, G. Schinkel and A. Lendlein, *Expert Rev Med Devic*, 2006, 3, 835-851.
58. S. Lin-Gibson, J. A. Cooper, F. A. Landis and M. T. Cicerone, *Biomacromolecules*, 2007, 8, 1511-1518
59. T. S. Karande, J. L. Ong and C. M. Agrawal, *Annals of Biomedical Engineering*, 2004, 32, 1728-1743.
60. D. W. Hutmacher, *J Biomat Sci-Polym E*, 2001, 12, 107-124.
61. A. Vats, N. S. Tolley, J. M. Polak and J. E. Gough, *Clinical Otolaryngology*, 2003, 28, 165-172.
62. V. Karageorgiou and D. Kaplan, *Biomaterials*, 2005, 26, 5474-5491
63. C. Erisken, D. M. Kalyon and H. Wang, *Biomaterials*, 2008, 29, 4065-4073.
64. C. Erisken, D. M. Kalyon and H. Wang, *Nanotechnology*, 2008, 19, 165302.
65. C. Erisken, D. M. Kalyon and H. Wang, *J Biomech Eng*, 2010, 132, 091013.
66. S. Ozkan, D. M. Kalyon and X. Yu, *J Biomed Mater Res A*, 2010, 92, 1007-1018.
67. S. Ozkan, D. M. Kalyon, X. Yu, C. A. McKelvey and M. Lowinger, *Biomaterials*, 2009, 30, 4336-4347
68. A. Ergun, X. Yu, A. Valdevit, A. Ritter and D. M. Kalyon, *J Biomed Mater Res A*, 2011, 99, 354-366.
69. A. Ergun, X. Yu, A. Valdevit, A. Ritter and D. M. Kalyon, *Tissue engineering. Part A*, 2012, 18, 2426-2436.
70. C. O'Brien, B. Holmes, S. Faucett and L. G. Zhang, *Tissue Eng Part B Rev*, 2015, 21, 103-114.
71. B. Holmes, W. Zhu, J. Li, J. D. Lee and L. G. Zhang, *Tissue Eng Part A*, 2015, 21, 403-415.
72. S. Ichinose, K. Yamagata, I. Sekiya, T. Muneta and M. Tagami, *Clinical and experimental pharmacology & physiology*, 2005, 32, 561-570.
73. W. G. Bian, D. C. Li, Q. Lian, X. Li, W. J. Zhang, K. Z. Wang and Z. M. Jin, *Rapid Prototyping J*, 2012, 18, 68-80.
74. S. V. Murphy, A. Skardal and A. Atala, *J Biomed Mater Res A*, 2013, 101A, 272-284.
75. N. J. 77 Castro, R. Patel and L. Zhang, *Cellular and Molecular Bioengineering*, 2015, 1-17
76. A. Baji, 78 S. C. Wong, T. S. Srivatsan, G. O. Njus and G. Mathur, *Mater Manuf Process*, 2006, 21, 211-218.
77. D. G. Marchesi, *Eur Spine J*, 2000, 9, 372-378.
78. C. Piconi and G. Maccauro, *Biomaterials*, 1999, 20, 1-25
79. C. D. Friedman, P. D. Costantino, S. Takagi and L. C. Chow, *Journal of Biomedical Materials Research*, 1998, 43, 428-432.
80. I. Sopyan, M. Mel, S. Ramesh and K. A. Khalid, *Science and Technology of Advanced Materials*, 2007, 8, 116-123.
81. Y. K. Hwang, U. Jeong and E. C. Cho, *Langmuir*, 2008, 24, 2446-2451.

82. L. Zhang, Y. Chen, J. Rodriguez, H. Fenniri and T. J. Webster, *International Journal of Nanomedicine*, 2008, 3, 323-333.
83. L. Sun, L. Zhang, U. D. Hemraz, H. Fenniri and T. J. Webster, *Tissue engineering. Part A*, 2012, 18, 1741-1750.
84. E. S. Place, J. H. George, C. K. Williams and M. M. Stevens, *Chemical Society reviews*, 2009, 38, 1139-1151.
85. L. Zhang and T. J. Webster, *Nanotoday*, 2009, 4, 66-80.
86. J. Li, J. D. Lee and K. P. Chong, *International Journal of Smart and Nano Materials*, 2011, 3, 2-13.
87. D. Moreau, A. Villain, D. N. Ku and L. Corte, *Biomatter*, 2014, 4, e28764.
88. K. Matsumura, T. Hayami, S. H. Hyon and S. Tsutsumi, *J Biomed Mater Res A*, 2010, 92, 1225-1232.
89. K. Madhumathi, K. T. Shalumon, V. V. Rani, H. Tamura, T. Furuike, N. Selvamurugan, S. V. Nair and R. Jayakumar, *International journal of biological macromolecules*, 2009, 45, 12-15.
90. L. C. Wu, J. Yang and J. Kopecek, *Biomaterials*, 2011, 32, 5341-5353.
91. A. Sugino, T. Miyazaki and C. Ohtsuki, *Journal of materials science. Materials in medicine*, 2008, 19, 2269-2274.
92. T. Iwatsubo, K. Sumaru, T. Kanamori, T. Shinbo and T. Yamaguchi, *Biomacromolecules*, 2006, 7, 95-100.
93. H. K. Makadia and S. J. Siegel, *Polymers*, 2011, 3, 1377-1397
94. S. P. Zustiak and J. B. Leach, *Biomacromolecules*, 2010, 11, 1348-1357.
95. J. Knychala, N. Bouropoulos, C. J. Catt, O. L. Katsamenis, C. P. Please and B. G. Sengers, *Ann Biomed Eng*, 2013, 41, 917-930.
96. J. C. Schagemann, S. Paul, M. E. Casper, J. Rohwedel, J. Kramer, C. Kaps, H. Mittelstaedt, M. Fehr and G. G. Reinholz, *J Biomed Mater Res A*, 2013, 101, 1620-1628.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method of producing a biomimetic scaffold comprising:
    fabricating a plurality of first polymer-based core-shelled particles via a wet coaxial electrospray technique, wherein said plurality of first polymer-based core-shelled particles have an average size from 50 nm to 250 nm in diameter;
    preparing a first layer from a first composite comprising a first biocompatible polymer mixture and said plurality of first polymer-based core-shelled particles;
    preparing a second layer from a second composite comprising a second biocompatible polymer mixture, wherein said second layer is fabricated onto said first layer; and
    wherein said first polymer-based core-shelled particles encapsulate an aqueous phase comprising a first compound.

2. The method according to claim 1, wherein a custom co-axial needle system comprising an inner needle with a set diameter receded within an outer needle with a diameter greater than that of said inner needle is used to create said first polymer-based core-shelled particles.

3. The method according to claim 1, wherein the plurality of first polymer-based core-shelled particles are created from a polymer comprising polydioxanone, polyethylene glycol, poly lactic-co-glycolic acid, or any combination thereof.

4. The method according to claim 1, wherein said plurality of first polymer-based core-shelled particles are formed and collected in a stabilizing bath.

5. The method according to claim 1, wherein said first compound is bone-morphogenic protein-2 or transformation growth-factor-β1.

6. The method according to claim 1, wherein said first composite further comprises sodium chloride (NaCl).

7. The method according to claim 1, wherein said first composite further comprises nanocrystalline hydroxyapatite.

8. The method according to claim 1, wherein said first biocompatible polymer mixture, the second biocompatible polymer mixture, or both comprises polyethylene glycol, polyethylene glycol-diacrylate, polycaprolactone, or any combination thereof.

9. The method according to claim 1, wherein said biomimetic scaffold is subjected at least once to a porogen leaching step.

10. The method according to claim 1, further comprising fabricating a plurality of second polymer-based core-shelled particles via a wet coaxial electrospray technique, wherein said plurality of second polymer-based core-shelled particles have an average size from 50 nm to 250 nm.

11. The method according to claim 10, wherein said second polymer-based core-shelled particles encapsulate an aqueous phase comprising a second compound.

12. The method according to claim 11, wherein said first compound and said second compound are different.

13. The method according to claim 11, wherein said second composite comprises said second polymer-based core-shelled particles.

14. The method according to claim 1, wherein said preparing a first layer, said preparing a second layer, or both uses a three-dimensional printing technology.

* * * * *